US008741883B2

(12) United States Patent
Yang et al.

(10) Patent No.: US 8,741,883 B2
(45) Date of Patent: Jun. 3, 2014

(54) COMPOUNDS AND METHODS FOR THE DIAGNOSIS AND TREATMENT OF AMYLOID ASSOCIATED DISEASES

(75) Inventors: Jerry Yang, La Jolla, CA (US); Petra Inbar, San Diego, CA (US)

(73) Assignee: The Regents of the University of California—San Diego, La Jolla, CA (US)

( * ) Notice: Subject to any disclaimer, the term of this patent is extended or adjusted under 35 U.S.C. 154(b) by 875 days.

(21) Appl. No.: 12/687,070

(22) Filed: Jan. 13, 2010

(65) Prior Publication Data

US 2010/0178282 A1 Jul. 15, 2010

Related U.S. Application Data

(62) Division of application No. 11/487,224, filed on Jul. 14, 2006, now Pat. No. 7,666,886.

(60) Provisional application No. 60/750,422, filed on Dec. 13, 2005, provisional application No. 60/699,726, filed on Jul. 15, 2005.

(51) Int. Cl.
*A61K 31/33* (2006.01)
*A61K 31/425* (2006.01)

(52) U.S. Cl.
USPC .......................................... 514/183; 514/367

(58) Field of Classification Search
None
See application file for complete search history.

(56) References Cited

U.S. PATENT DOCUMENTS 6,479,528 B1  11/2002  Kuret et al.
6,696,039 B2   2/2004  Kung et al.

OTHER PUBLICATIONS

Fryer. Neuron, 2005, 47, 167-68.*
Blower, P.J., "Inorganic pharmaceuticals", Annual Report on the Progress of Chemistry, Section A, 1999, 95:631-55.
Inbar, Petra et al., "Oligo (ethylene glychol) derivatives of thioflavin T as inhibitors of pritein-amyloid interactions", ChemBioChem, 2006, 7(10):1563-6.
Ishikawa, K. et al., "Amyloid imaging probes are useful for detection of prion plaques and treatment of transmissible spongiform encephalopathies," Journal of General Virology (2004), 85:1785-90, Jun. 2004.
Levine, H., "Thioflavine T interaction with synthetic Alzheimer's disease β-amyloid peptides: detection of amyloid aggregation in solution," Protein Science (1993), 2:404-10, Cambridge University Press, USA, Mar. 1993.
Lockhart, A. et al., "Evidence for the presence of three distinct binding sites for the Thioflavin T class of Alzheimer's disease PET imaging agents on β-amyloid peptide fibrils*," The Journal of Biological Chemistry, 280(9):7677-84, USA, Mar. 4, 2005.
Mashraqui, Sabir H. et al., "Aza-crown ether tethered with benzothiazole: synthesis and optical spectral studies", Indian Journal of Chemistry, Mar. 2006, 45B(3):815-9.
Mateeva, N. et al., "Synthesis and spectral properties of a new benothiazolic chromofluoroionophore containing the aza-15-crown-5 macrocyclic moity", Journal of Inclusion Phenomena and Molecular Recognition in Chemistry, 1994, 17:81-91.
Yan, S. et al., "Amyloid-β peptide-receptor for advanced glycation endproduct interaction elicits neuronal expression of macrophage-colony stimulating factor: a proinflammatory pathway in Alzheimer disease," Proc. Natl. Acad. Sci. USA, 94:5296-301, May 1997.

\* cited by examiner

*Primary Examiner* — Noble Jarrell
(74) *Attorney, Agent, or Firm* — Kilpatrick Townsend & Stockton LLP

(57) ABSTRACT

The invention is in general directed to compounds and methods for diagnosing, preventing or alleviating the symptoms of amyloid-associated diseases, for example, neuronal diseases, such as, for example, Alzheimer's disease, methods of screening for compounds useful in preventing or alleviating the symptoms of amyloid-associated diseases, methods of diagnostic imaging of A-beta fibrils, and compounds and methods useful for studying normal or disease-associated cellular mechanisms relating to amyloid proteins.

7 Claims, 12 Drawing Sheets

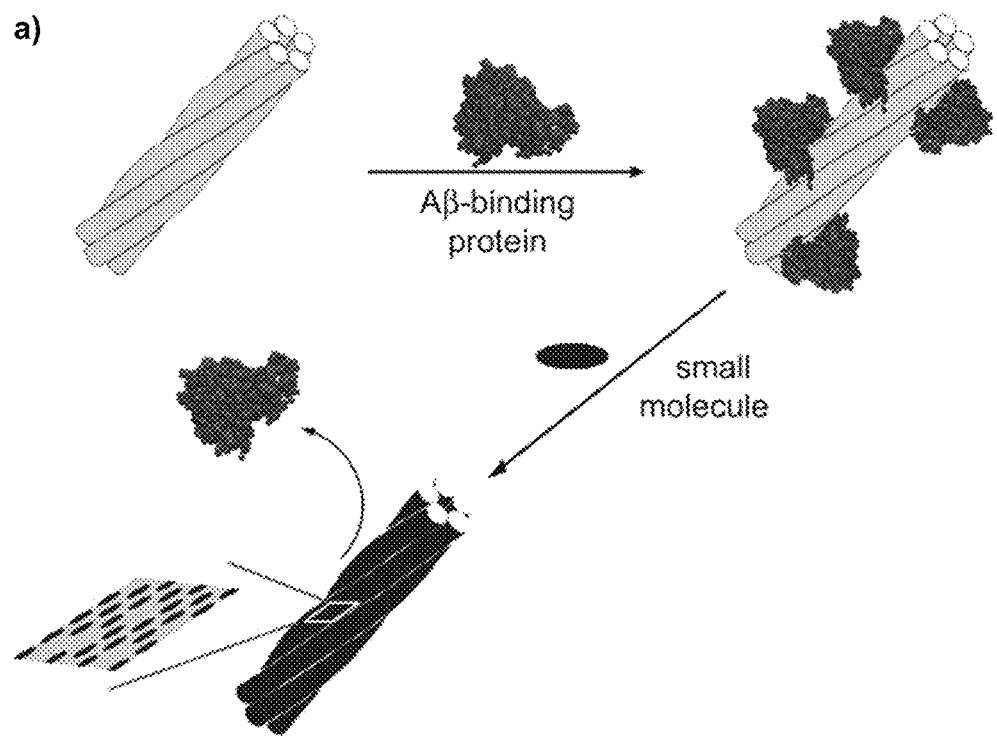
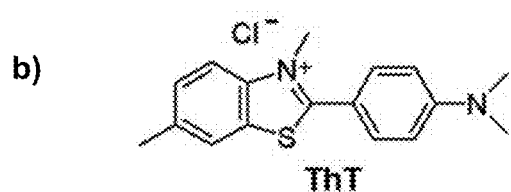
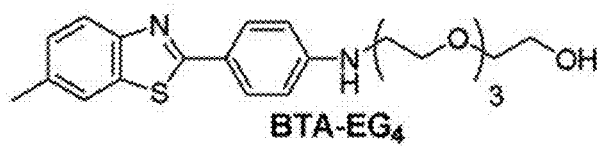
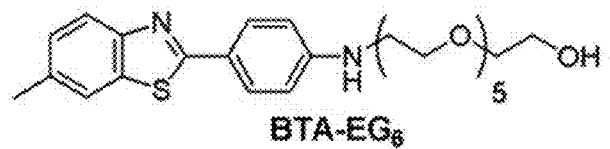
FIGURE 1

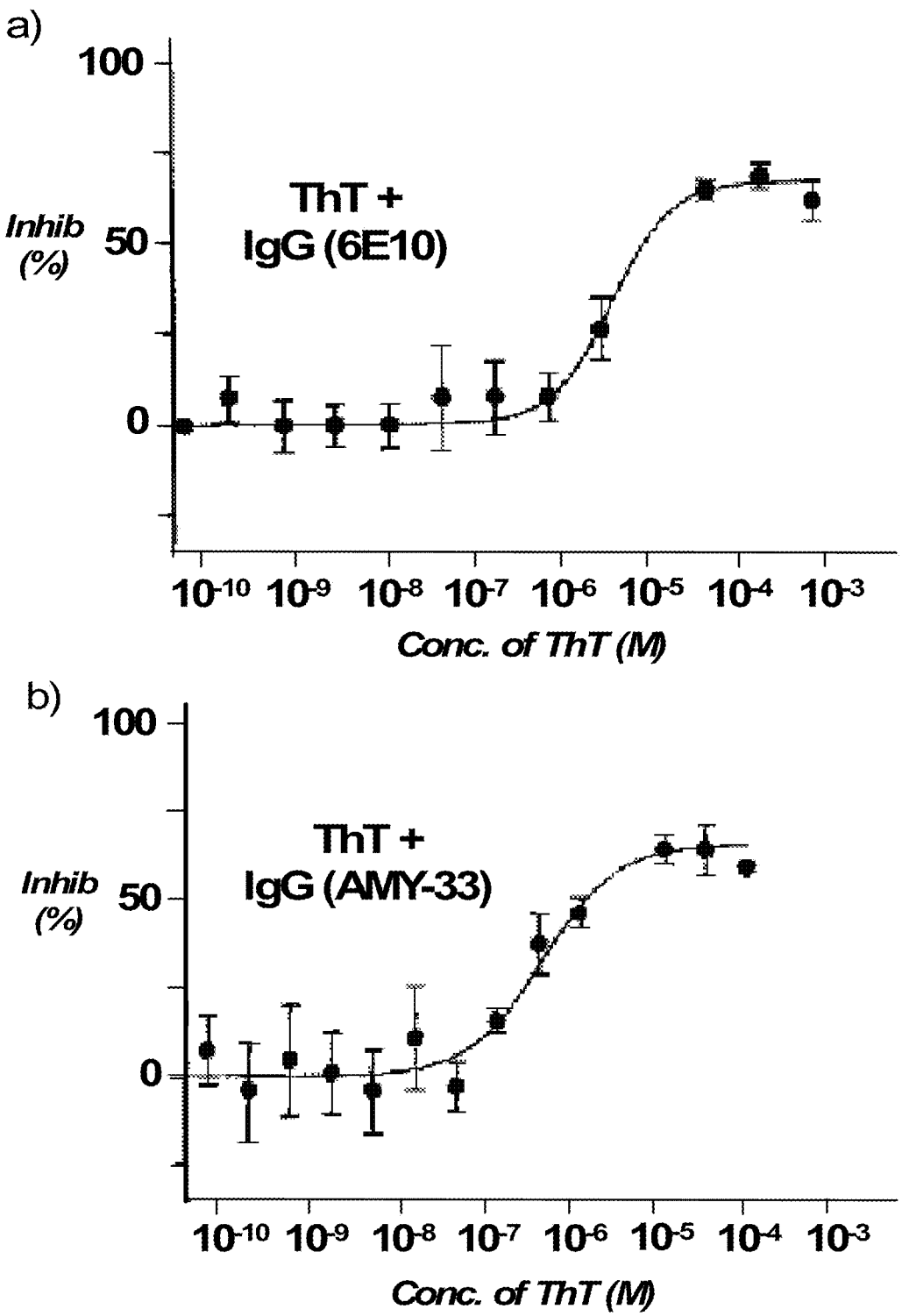
FIGURES 2a-b

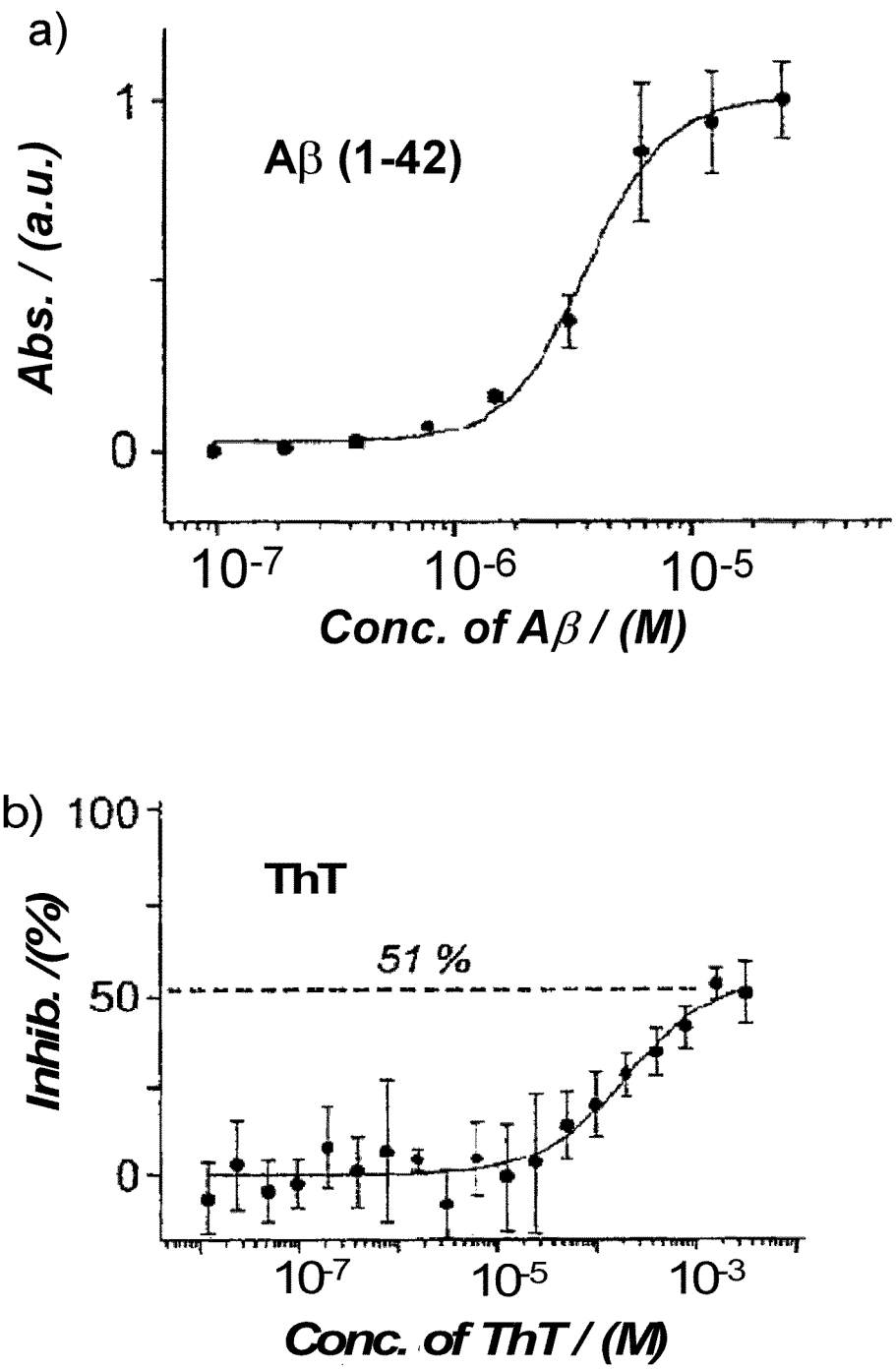
FIGURES 6a-b

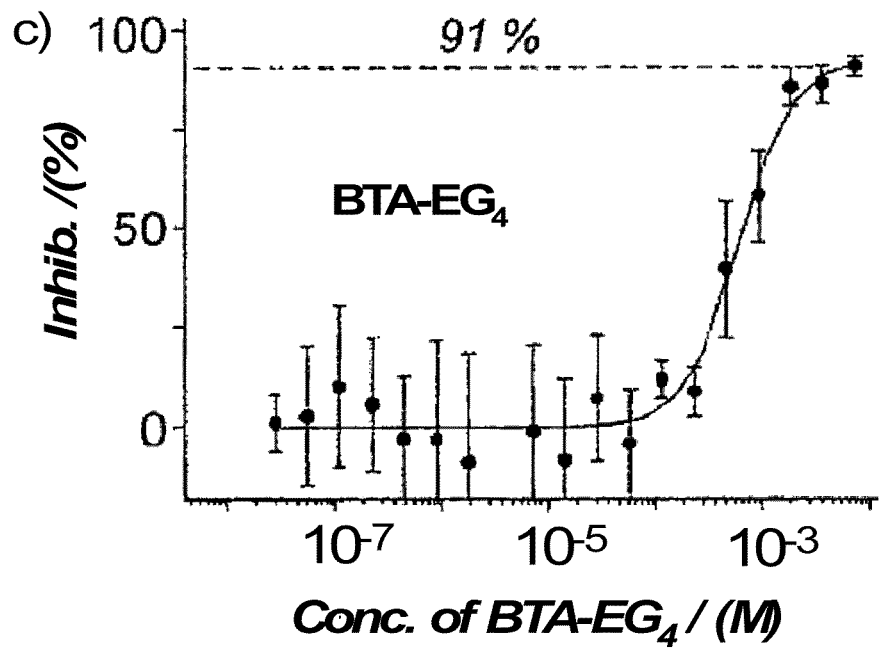
FIGURES 6c-d

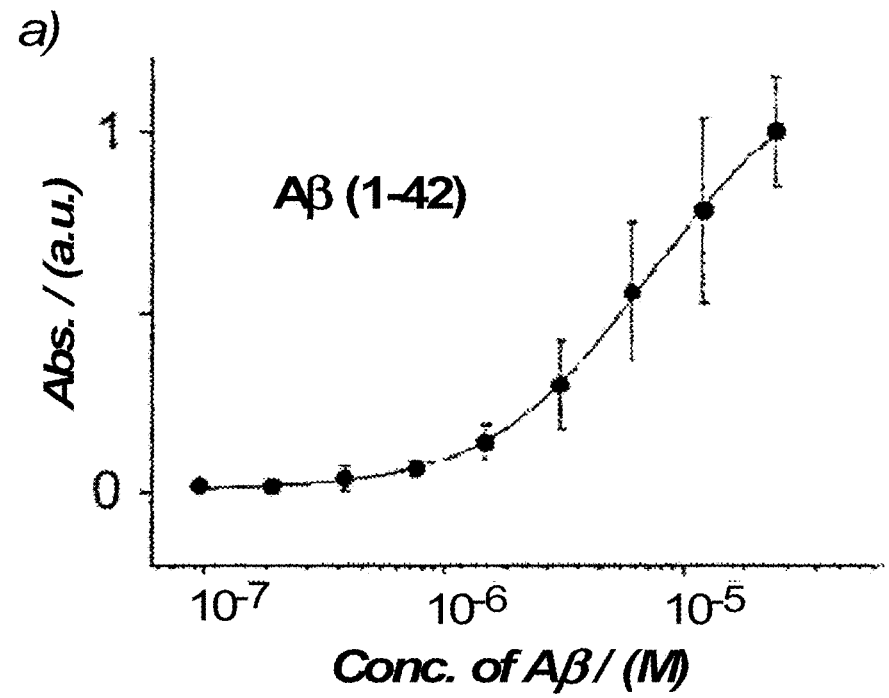
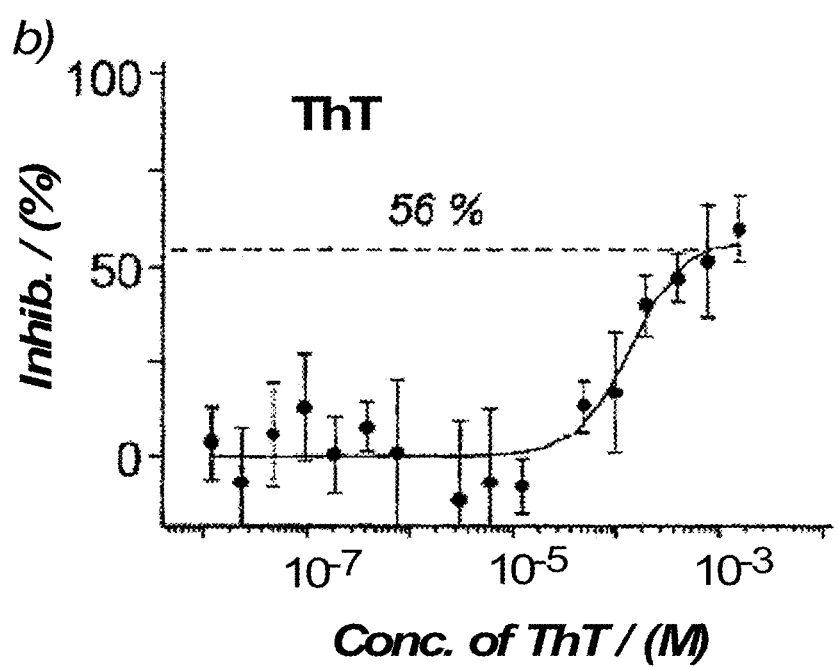
FIGURES 7a-b

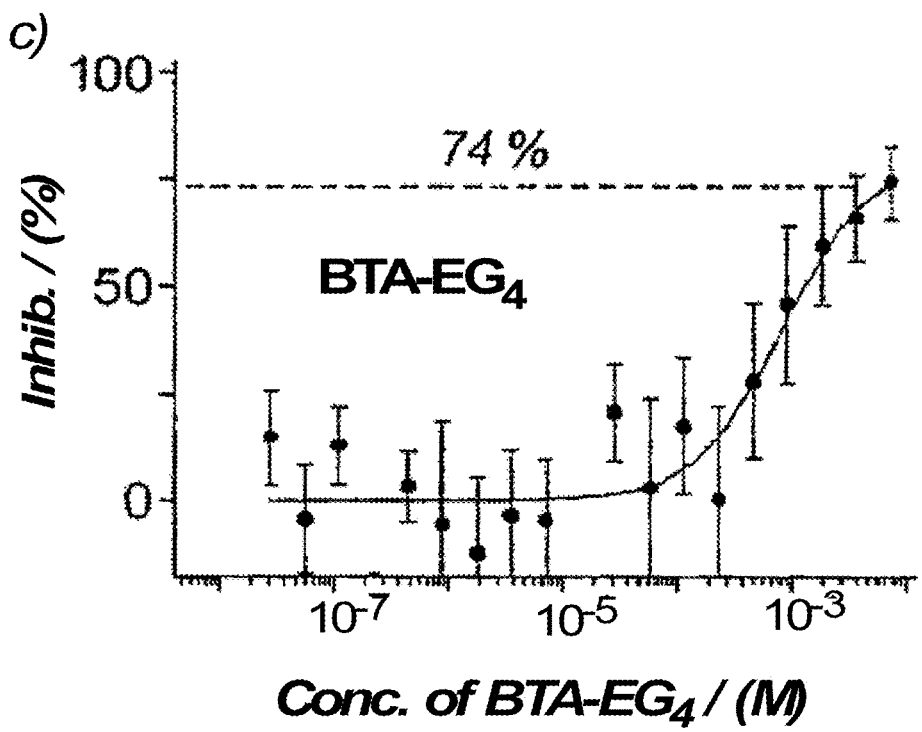
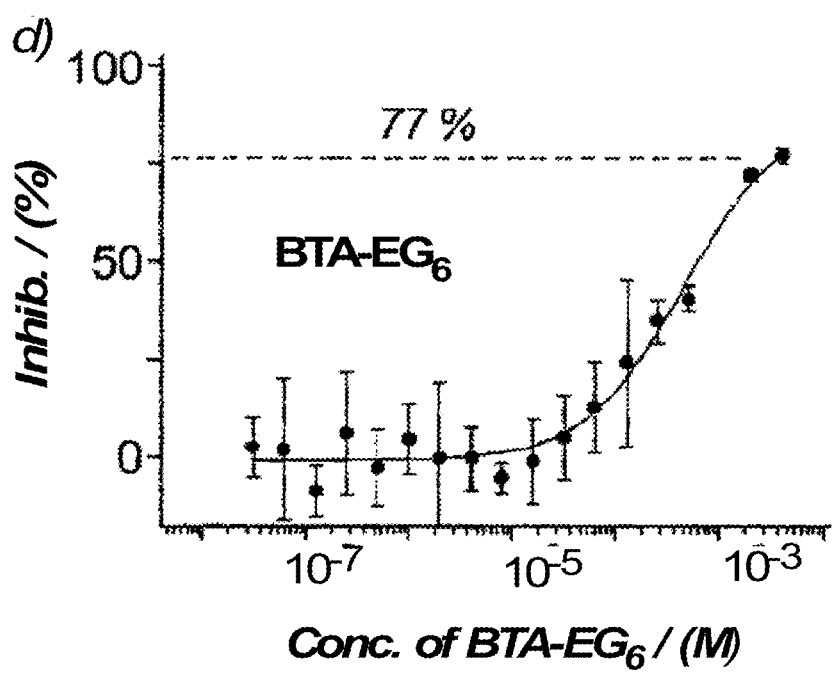
FIGURES 7c-d

COMPOUNDS AND METHODS FOR THE DIAGNOSIS AND TREATMENT OF AMYLOID ASSOCIATED DISEASES

PRIORITY

Priority is claimed to U.S. application Ser. No. 11/487,224, now issued as U.S. Pat. No. 7,666,886, which in turn claims priority to U.S. Provisional Application Ser. No. US 60/699,726, filed Jul. 15, 2005, and entitled New Approach for Therapeutics for Alzheimer's Disease; and U.S. Provisional Application Ser. No. US 60/750,422, filed Dec. 13, 2005, and entitled Compounds and Methods for the Diagnosis and Treatment of Alzheimer's Disease, each of which are referred to and incorporated herein by reference in their entirety.

FIELD OF THE INVENTION

The invention is in general directed to compounds and methods for diagnosing, preventing or alleviating the symptoms of amyloid-associated diseases, for example, neuronal diseases, such as, for example, Alzheimer's disease, methods of screening for compounds useful in preventing or alleviating the symptoms of amyloid-associated diseases, methods of diagnostic imaging of A-beta fibrils, and compounds and methods useful for studying normal or disease-associated cellular mechanisms relating to amyloid proteins.

BACKGROUND

Amyloid fibrils formed from misfolded proteins or peptides are a hallmark of many neuronal diseases, such as, for example, Alzheimer's disease. (Soto, C. Nature Rev. Neurosci. 2003, 4: 49; Agorogiannis, E. I., et al., Neuro path. Appl. Neurobiol. 2004, 30:215; Kelly, J. W. Structure 1997, 5:595.) Amyloid fibrils have also been associated with other, non-neuronal diseases and conditions, such as, for example, those listed in Table 1.

Amyloid fibrils and plaques are rich in beta sheet structure. A-beta is a peptide found in amyloid fibrils and plaques. Researchers have associated the development of Alzheimer's disease (AD), with the interaction of A-beta peptides, oligomers, and fibrils with cellular components in the brain. (Dawbarn, D., and Allen, S. J. Neurobiology of Alzheimer's disease, second ed., Oxford University Press, Oxford, 2001; Pereira, C., et al., J. Mol. Neurosci. 2004, 23: 97.) The interaction between cellular proteins, such as, for example, catalase, ABAD (beta amyloid-binding alcohol dehydrogenase) and RAGE (receptor for advanced glycation end products) and aggregated A-beta-amyloid fibrils (A-beta fibrils), for example, have been reported for their potential contribution to A-beta-induced neurotoxicity in the pathogenesis of AD. (Milton, N. G. N. Biochem. J. 1999, 344:293-296; Milton, N. G. N., et al. Neuroreport 2001, 121: 2561; Yan, S. D., et al. Nature 1997, 389: 689; Yan, S. D., et al. J. Biol. Chem. 1999, 274: 2145; Lustbader, J. W., et al. Science 2004, 304: 448; Yan, S. D., et al. Nature 1996, 382: 685; Yan, S. D, et al., Am. J. Pathol. 1999, 155: 1403; Yan, S. D., et al., Biochim. Biophys. Acta 2000, 1502: 145; K. Takuma, J. Yao, J. Huang, H. Xu, X. Chen, J. Luddy, A.-C. Trillat, D. M. Stern, O. Arancio, S. S. Yan, *FASEB J.* 2005, 19(6), 597-598; Takuma, K., et al., FASEB J. 2005, 19(6): 597-598)

Several classes of small molecule therapeutics are used clinically to treat the symptoms of AD, such as, for example, inhibitors of cholinesterase. (Francis, P. T., et al, Trends Pharm. Sci. 2005, 26: 104; Conway, K. A., et al., Curr. Pharm. Design 2003, 9: 427.) Current strategies to modify directly the pathology of AD using synthetic molecules are focused mainly on slowing down the production of A-beta peptide or preventing the growth of A-beta fibrils. (C. Schmuck, et al., ChemBioChem 2005, 6: 1; C. N. Johnson, et al., Drug Dis. Today 2004, 1: 13; M. S. Parihar and T. Hemnani, J. Clin. Neurosci. 2004, 11: 456; V. M.-Y. Lee, Neurobio. Aging 2002, 23: 1039; B. Bohrmann, et al., J. Biol. Chem. 1999, 274: 15990; F. G. De Felice, et al., FASEB J. 2004, 18:1366; M. A. Findeis, Biochim. Biophys. Acta 2000, 1502:76; J. E. Gestwicki, et al., Science 2004, 306: 865).

Other strategies focus on disrupting the fibrils so that they disassemble into their A-beta peptide components. These approaches may increase the amount of A-beta peptide, A-beta-dimers, or small A-beta oligomers in neurons, which may have a toxic affect.

Thioflavin T (ThT) a fluorescent molecule (FIG. 1b)—is used extensively for the characterization of A-beta fibrils (LeVine III, H. Meth. Enzym. 1999, 309: 274.) and for the detection of aggregation of A-beta in solution. (Blanchard, B. J., et al., Proc. Nat. Acad. Sci. USA 2004, 101: 14326; Ono, K., et al., J. Neurochem. 2002, 81: 434.) Several groups have studied the interaction of ThT with A-beta fibrils by fluorescence and showed that ThT binds uniformly to the bulk of A-beta fibrils with high affinity ($K_d$'s ranging from high nM to low µM). (LeVine III, H. Protein Sci. 1993, 2: 404; LeVine III, H. Amyloid 1995, 2: 1; LeVine III, H. Arch. Biochem. Biophys. 1997, 342: 306; Lockhart, A., et al., J. Biol. Chem. 2005, 280: 7677; Krebs, M. R. H., et al., J. Struct. Biol. 2005, 149: 30). Thioflavin derivatives have been reported to be used in the diagnosis of Alzheimer's and in in vivo imaging, and Congo Red (CR) is used by researchers to stain amyloid plaques found in patients with Alzheimer's disease. (Klunk, W., et al., U.S. Patent Application Publication No. 20050043377 (2005); C. A. Mathis, et al., Current Pharm. Design, 2004, 10:1469-92; and Hintersteiner, M., et al., Nature Biotechnology, 2005, 23:577-83.)

Molecular coatings on metallic and polymeric surfaces are used frequently to attenuate interactions of proteins with artificial materials for biological studies and biotechnology applications. (Chapman, R. G., et al., J. Am. Chem. Soc. 2000, 122: 8303; Mrksich, M., et al., Proc. Nat. Acad. Sci. USA 1996, 93:10775; Chiu, D. T., et al., Proc. Nat. Acad. Sci. USA 2000, 97: 2408; Chen, X., et al., Langmuir 2002, 18: 7009; Siegers, C., et al., Chem. Eur. J. 2004, 10: 2831.)

There is a need for novel methods and compounds for diagnosing and treating amyloid-associated diseases, for example, neuronal diseases and conditions, with a smaller incidence of toxicity.

SUMMARY

Provided herein are compounds and methods for preventing or alleviating the symptoms of amyloid-associated diseases, for example, but not limited to, neuronal diseases and conditions associated with amyloid fibril or plaque formation. It has been found that providing a binding molecule that coats the surface of an A-beta fibril may allow the fibrils to resist the interaction of cellular proteins with these fibrils, resulting in a new strategy to intervene in AD-related pathology. Provided herein are compounds that inhibit the binding interaction between A-beta fibrils and cellular proteins. In other embodiments are provided methods of screening for compounds useful in preventing or alleviating the symptoms of neuronal diseases, and methods of diagnostic imaging of A-beta fibrils.

In a first embodiment of the present invention is provided a compound of formula I:

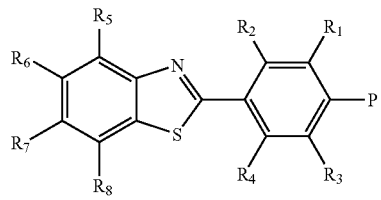

wherein $R_1$-$R_8$ are selected from the group consisting of hydrogen, deuterium, tritium, fluoride, chloride, bromide, iodide, hydroxide, amino, methylamino, dimethylamino, trimethylammonium, methyl, ethyl, methoxy, ethoxy, fluoromethyl, difluoromethyl, trifluoromethyl, wherein at least one of R5-R8 and one of $R_1$-$R_4$ is H; and P is selected from the group consisting of

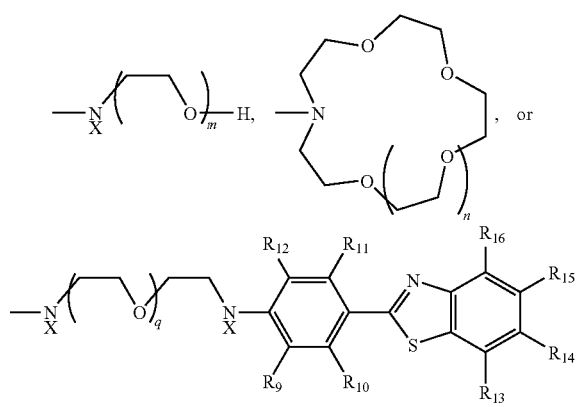

wherein
m is an integer between 1 and 20;
n is 0, 1, or 2;
q is an integer between 1 and 20;
$R_9$-$R_{16}$ are selected from the group consisting of hydrogen, deuterium, tritium, fluoride, chloride, bromide, iodide, hydroxide, amino, methylamino, dimethylamino, trimethylammonium, methyl, ethyl, methoxy, ethoxy, fluoromethyl, difluoromethyl, trifluoromethyl, wherein at least one of $R_9$-$R_{12}$ and one of $R_{13}$-$R_{16}$ is H; and
X is hydrogen, methyl, or ethyl.

In further embodiments, P, for example, is

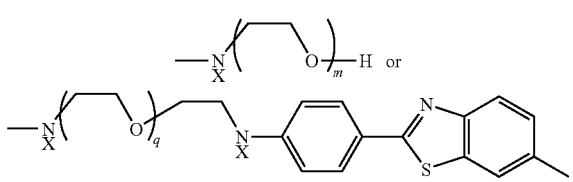

In exemplary embodiments of the present invention, for example, m is an integer between 3 and 16, 3 and 12, 5 and 10, 6 and 10, 3 and 7, 4 and 7, or 3 and 8. By "between" in the context of the present invention, is meant to include both the first and second numbers. Thus, "between 4 and 6" is meant to include 4, 5, and 6. In exemplary embodiments, m is 4, for example, or m is 6, for example. In other exemplary embodiments, $R_1$-$R_{16}$ are H. In exemplary embodiments of the present invention, the compound is BTA-EG$_4$, BTA-EG$_6$, BTA-Aza-Crown$_5$, or BTA-EG$_6$-BTA. By "compound of the present invention" is meant a compound of formula I, including, for example, each of the embodiments of such compounds.

In other examples of the present invention, P is

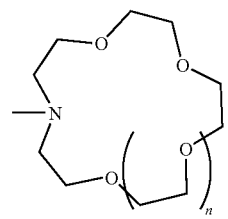

and n is 1.

The present invention further provides pharmaceutical compositions comprising a pharmaceutically acceptable excipient and any of the compounds of the present invention.

Also provided in the present invention is a method of preventing or alleviating the symptoms of an amyloid associated disease comprising contacting A-beta fibrils with a compound of the present invention. In exemplary embodiments, the disease is a neuronal disease. In further exemplary embodiments, the neuronal disease is selected from the group consisting of Alzheimer's disease, Parkinson's disease, Huntington's disease Down's Syndrome, and spongiform encephalopathy. For example, the neuronal disease may be, but is not limited to, Alzheimer's disease. Or, for example, the neuronal disease may be, but is not limited to, Parkinson's disease.

Also provided in the present invention is a method of preventing or alleviating the symptoms of an amyloid associated disease comprising contacting A-beta fibrils with a sufficient amount of a first binding molecule to decrease the interactions of the A-beta fibrils with a second binding molecule. In certain embodiments, the disease is a neuronal disease. In certain embodiments, a plurality of the first binding molecules forms an ordered layer on top of the fibrils. For example, the first binding molecule may coat a portion of the surface of the fibrils. The first binding molecule may, for example, coat more than 50, 55, 60, 65, 70, 75, 80, 85, 90, or 95% of the surface of the fibrils. The second binding molecule may be, for example a cellular component in the brain. The second binding molecule may be, for example, a cellular protein. The second binding molecule may be, for example, selected from the group consisting of catalase, ABAD, and RAGE. In certain embodiments of the present invention, the binding of the second binding molecule to the fibrils is associated with the symptoms of an amyloid associated disease, such as, for example, those listed in Table 1. In other embodiments of the present invention, the binding of the second binding molecule to the fibrils is associated with the symptoms of a neuronal disease, such as, for example, Alzheimer's disease, Parkinson's disease, Huntington's disease Down's Syndrome, or spongiform encephalopathy. In exemplary embodiments, the neuronal disease is Alzheimer's disease. In other exemplary embodiments, the neuronal disease is Parkinson's disease.

In some aspects of the present invention, the first binding molecule binds to the fibrils using hydrophobic and electrostatic interactions. In other aspects, the first binding molecule binds to the fibrils using non-covalent interactions with the fibrils. In certain aspects of the invention, the first binding molecule is selected from the group consisting of Congo Red, a Congo Red derivative, Thioflavin T, and a Thioflavin T derivative. In other aspects of the invention, the first binding molecule is a compound of the present invention. In further embodiments of the invention, the method comprises administering a therapeutically effective amount of the first binding molecule to an individual. By "individual" is meant, for example, any animal, for example, any mammal, such as, for example, a bovine, rodent, primate, horse, canine, feline, or human. In exemplary embodiments, the individual is human.

Also provided in the present invention is a method of screening for a compound that blocks the binding of an A-beta fibril binding molecule to A-beta fibrils, comprising Depositing A-beta fibrils onto a test surface.

Adding a test compound to the A-beta fibrils and incubating the deposited fibrils with the test compound;

Adding an A-beta fibril binding molecule to the test surface;

Determining the amount of the binding molecule that binds the fibrils; and

Determining if the test compound decreases the binding of the binding molecule to the fibrils.

In other embodiments of the present invention is provided a method of screening for a compound that blocks the binding of an A-beta-fibril binding molecule to A-beta fibrils, comprising Incubating A-beta fibrils with a test compound;

Depositing the test-compound-incubated A-beta fibrils onto a test surface;

Adding an A-beta fibril binding molecule to the test surface;

Determining the amount of the binding molecule that binds the fibrils; and

Determining if the test compound decreases the binding of the binding molecule to the fibrils.

The compounds of the present invention may also be used for diagnostic imaging of A-beta fibrils. The methods of the present invention also provide methods for screening for compounds useful for diagnostic imaging of A-beta fibrils, comprising, for example, Depositing A-beta fibrils onto a test surface;

Adding a test compound to the A-beta fibrils and incubating the deposited fibrils with the test compound;

Adding an A-beta fibril binding molecule to the test surface;

Determining the amount of the binding molecule that binds the fibrils; and

Determining if the test compound decreases the binding of the binding molecule to the fibrils.

In other embodiments of the present invention is provided a method of screening for a compound used for diagnostic imaging of A-beta fibrils, comprising Incubating A-beta fibrils with a test compound;

Depositing the test-compound-incubated A-beta fibrils onto a test surface;

Adding an A-beta fibril binding molecule to the test surface;

Determining the amount of the binding molecule that binds the fibrils; and

Determining if the test compound decreases the binding of the binding molecule to the fibrils.

The test surface may be, for example, a test well. The test well, may be, for example, present in a microtiter plate. The A-beta fibril binding molecule, in exemplary embodiments, may be, for example, selected from the group consisting of an antibody, RAGE, ABAD, and catalase. For example, the antibody may be an anti-A-beta antibody. Determining the amount of A-beta fibril binding molecule that binds the fibrils may be conducted, for example, using an ELISA assay. In certain aspects of the method, prior to adding the test compound to the well, the test compound is pre-incubated with A-beta-fibrils. Those of ordinary skill in the art will understand that various concentrations of the test compound may be tested in the screening, and that determining whether the test compounds decreases binding of a binding molecule to the fibrils may be conducted by comparing the amount of binding of the binding molecule to the fibrils in the presence and in the absence of the test compound. This may also include, for example, comparing the amount of binding of the binding molecule to the fibrils in the presence of at least two different concentrations of the test compound. In certain exemplary screening embodiments, the A-beta fibril binding molecule is an isolated brain cellular component, for example, a component selected from the group consisting of catalase, ABAD, and RAGE. The test compound may be, for example, a compound of the present invention.

In yet other embodiments of the present invention are provided methods for diagnosing an amyloid associated disease in an individual, comprising administering an A-beta fibril-binding compound to an individual and detecting the binding of the compound to amyloid deposits in the individual, wherein the compound is selected from the group consisting of a compound of any of claims 1-6, Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof. In exemplary embodiments, the amyloid associated disease is a neuronal disease. In further exemplary embodiments, the compound is a compound of the present invention.

In further embodiments of the present invention are provided methods for identifying a change in the progress of an amyloid associated disease in an individual, comprising administering an A-beta fibril-binding compound to an individual and conducting a first detecting procedure to detect the binding of the compound to amyloid deposits in the individual on a first date;

administering an A-beta fibril binding compound to the individual and conducting a second detecting procedure to detect the binding of the compound to amyloid deposits in the individual on a second date; and comparing the amount, quantity, or other characteristics of the amyloid deposits detected in step b with the amyloid deposits detected in step a, wherein the A-beta fibril binding compound is selected from the group consisting of a compound of the present invention, Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof. In exemplary embodiments, the disease is a neuronal disease. In certain embodiments, the compound is selected from the group consisting of a compound of the present invention, Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-

Catechin, (−)-Nicotine, Morin, Serotonin, Dopamine, Curcumin, (R)-Ibuprofen, (S)-Naproxen, Rifampin, D-(+)-Trehalose, D-nicotine, and pegylated derivatives of 1-(p-aminophenyl)-6-methylbenzothiazole. In exemplary embodiments, the compound is a compound of the present invention.

In yet further embodiments of the present invention are provided methods for detecting amyloid deposits in an individual, comprising
administering a pharmaceutical composition comprising a pharmaceutically acceptable carrier and a compound selected from the group consisting of a compound of the present invention, Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof; and
detecting the binding of the compound to an amyloid deposit in the individual. In exemplary embodiments, the pharmaceutical composition comprises a compound of the present invention. In certain embodiments, the amyloid deposit is present in the brain of the individual.

For detecting the presence of amyloid deposits, for example, the A-beta fibril-binding compound may be, for example, radiolabeled. Detection may be conducted by a method, for example, selected from the group consisting of gamma imaging, magnetic resonance imaging, or magnetic resonance spectroscopy. The detection may be, for example, single photon emission computed tomography or positron emission tomography.

In other embodiments of the present invention are provided methods for preventing or alleviating the symptoms of an amyloid associated disease comprising contacting A-beta fibrils with a sufficient amount of a pharmaceutical composition comprising a pharmaceutically acceptable carrier and an A-beta fibril binding compound selected from the group consisting of a compound of the present invention, Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof, to decrease the interactions of the A-beta fibrils with a second binding molecule. In exemplary embodiments, the disease is a neuronal disease. In exemplary embodiments, the pharmaceutical composition comprises a compound of the present invention.

In other embodiments of the present invention are provided methods for preventing or alleviating the symptoms of an amyloid associated disease in an individual comprising administering to the individual a therapeutically effective dose of a pharmaceutical composition comprising a pharmaceutically acceptable carrier and an A-beta fibril binding protein selected from the group consisting of a compound of the present invention, Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof, in a pharmaceutically acceptable carrier. In exemplary embodiments, the disease is a neuronal disease. In exemplary embodiments, the pharmaceutical composition comprises a compound of the present invention. The neuronal disease may be, for example, Alzheimer's disease; the neuronal disease may be, for example, Parkinson's disease.

In other exemplary embodiments of the present invention is provided a composition comprising a compound bound to one or more A-beta fibrils, wherein the compound is selected from the group consisting of a compound of the present invention, Fluoroscein, Diamino Acridine, Crystal Violet, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof. In exemplary aspects, the compound is a compound of the present invention.

Also provided in the present invention are research reagents comprising a compound of the present invention. The research reagent may be, for example, formulated to detect amyloid proteins in vivo. The research reagent may be, for example, formulated to detect amyloid proteins in cells or tissue, wherein the cells or tissue have been isolated from a living organism. Also provided in the present invention is a kit comprising a research reagent of the present invention.

BRIEF DESCRIPTION OF THE DRAWINGS

FIG. 1. Illustration of the inhibition of binding of Aβ-binding proteins to Aβ fibrils using small molecules. a) In this cartoon, the small molecules compete with the Aβ-binding proteins for binding to the Aβ fibril (see Puchtler, H., et al., J. Histochem. Cytochem. 1962, 10: 355; LeVine III., H. Meth. Enzym. 1999, 309: 274); b) chemical structures of Thioflavin T (ThT) and two derivatives of 2-(4-aminophenyl)-benzothiazoles (BTA-EG$_4$ and BTA-EG$_6$).

FIG. 6. Inhibition (Inhib.) of catalase-Aβ fibril interactions using small molecules. a) Binding of Aβ fibrils to catalase. Inhibition of catalase-Aβ fibril interactions with solutions of b) ThT; c) BTA-EG$_4$; and d) BTA-EG$_6$. Note: the x-axis was plotted in a logarithmic scale for better visualization of the data.

FIG. 7. Inhibition (Inhib.) of ABAD-Aβ fibril interactions using small molecules. a) Binding of Aβ-fibrils to ABAD. Inhibition of ABAD-Aβ fibril interactions with solutions of b) ThT; c) BTA-EG$_4$; and d) BTA-EG$_6$. Note: the x-axis was plotted in a logarithmic scale for better visualization of the data.

DETAILED DESCRIPTION

Figure 2C:
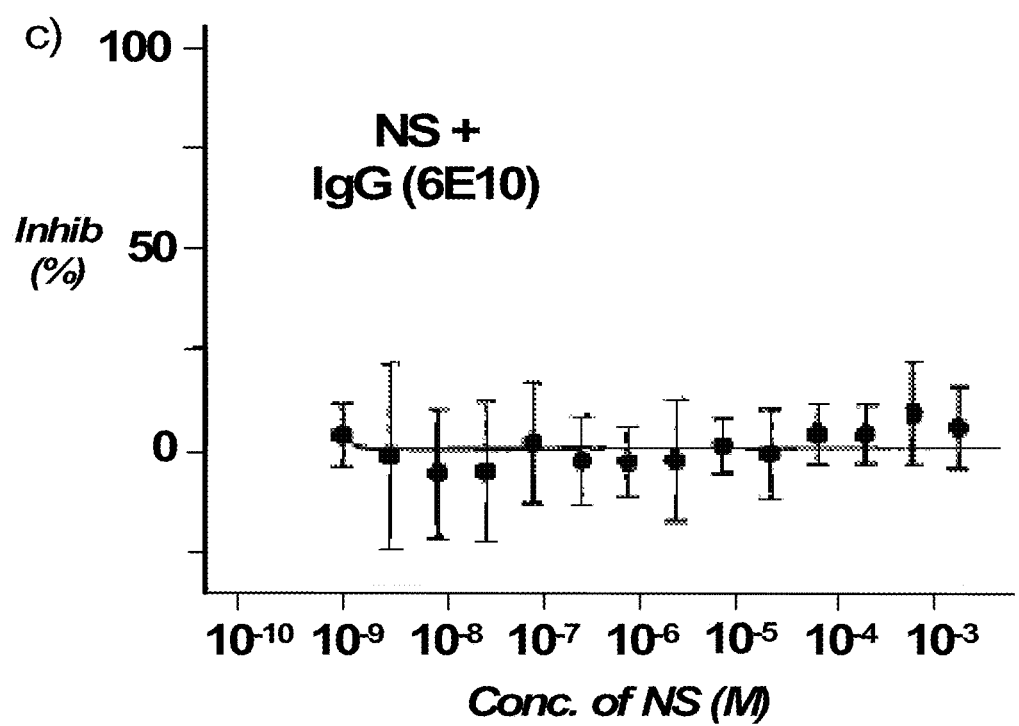
FIG. 2. Inhibition (Inhb.) of IgG-A-beta interactions with ThT. a) A-beta fibrils incubated with solutions of ThT and exposed to an anti-A-beta IgG (clone 6E10). b) Same assay as in (a) but using an anti-A-beta IgG raised against a different binding epitope of A-beta peptide (clone AMY-33). c) Same assay as in (a) except the inhibition is plotted against the concentration of 1-naphthol-4-sulfonate (NS) instead of ThT.
Figure 3:
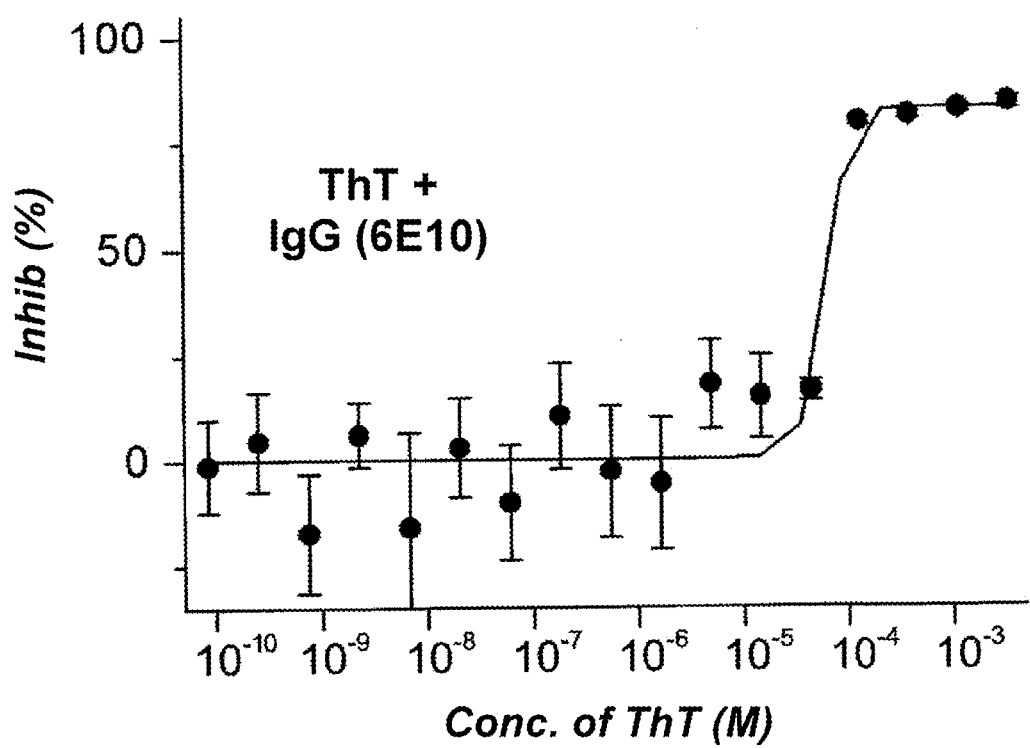
FIG. 3. Inhibition (Inhb.) of IgG-A-beta interactions as a function of increasing concentrations (conc.) of ThT. ThT and the fibrils were incubated together prior to depositing the ThT-coated fibrils into 96-well plates and exposure to an anti-A-beta IgG (clone 6E10, derived from A-beta residues 3-8 as antigens).

Provided herein are compounds and methods for diagnosing, preventing or alleviating the symptoms of amyloid-associated diseases, for example, diseases listed in Table 1. In exemplary embodiments are provided compounds and methods for diagnosing, preventing, or alleviating the symptoms of neuronal diseases, such as, for example, Alzheimer's disease, methods of screening for compounds useful in preventing or alleviating the symptoms of amyloid-associated diseases, methods of diagnostic imaging of A-beta fibrils, and compounds and methods useful for studying normal or disease-associated cellular mechanisms relating to amyloid proteins.

Diseases

By "amyloid associated diseases" is meant any disease or condition that is associated with the increased or decreased presence of amyloid proteins, such as the presence of amyloid plaques. The methods of the present invention may be used to diagnose or to detect a propensity for an amyloid-associated disease where no plaques are detected, such as, for example, by detecting amyloid protein as a biomarker. For example, the presence of amylin may be detected using the methods of the present invention, and this may be associated, for example, with a likelihood of developing type-two diabetes. Examples of amyloid associated diseases may be found in, but are not limited to, for example, Table 1.

Neuronal diseases that may be diagnosed, treated, prevented or exhibit an alleviation of symptoms according to the present invention include any neuronal disease or condition, including, for example, neurodegenerative diseases, in which A-beta peptides, oligomers, fibrils, or plaques are implicated, for example, but not limited to, Alzheimer's disease, Parkinson's disease, Huntington's disease, Down's Syndrome, and spongiform encephalopathies such as, for example, Bovine Spongiform Encephalopathy (mad cow disease), Kuru, Creutzfeldt-Jakob disease, and Fatal Familial Insomnia.

TABLE 1

| Amyloid | Disease | Reference |
|---|---|---|
| Amylin | Type 2 Diabetes | Goldsbury, C. S., et al., J Struc. Biol. 1997, 119(1), 17-27; Goldsbury, C., et al., J. Struc. Biol. 2000, 130(2-3), 352-362; Jimenez, J. L., et al., Proc. Natl. Acad. Sci. 2002, 99(14), 9196-9201. |
| Insulin | Type 2 Diabetes | Sipe, J. D., Ann. Rev. Biochem. 1992, 61, 947-975 |

TABLE 1-continued

| Amyloid | Disease | Reference |
|---|---|---|
| Immunoglobin light chains | AL amyloidosis (liver) | Bellotti, V., et al., J. Struc. Biol. 2000, 130(2-3), 280-289; Sipe, J. D., Ann. Rev. Biochem. 1992, 61, 947-975 |
| Amyloid A (Lipoprotein) | Reactive systemic amyloidosis | Sipe, J. D., Ann. Rev. Biochem. 1992, 61, 947-975 |
| Transthyretin | senile systemic amyloidosis (SSA), familial amyloid polyneuropathy (FAP) and familial amyloid cardiomyopathy (FAC) | Sipe, J. D., Ann. Rev. Biochem. 1992, 61, 947-975; Brito, R. M. M. et al., Curr. Med. Chem. Immun. Endoc. Metab. Agents 2003, 3(4), 349-360; Damas, A. M. and Saraiva, M. J., J. Struc. Biol. 2000, 130(2-3), 290-299; Buxbaum, J. N., Curr. Opin. Rheumatol. 2003, 16(1), 67-75. |
| β2 microglobulin | Dialysis, renal failure | Buxbaum, J. N., Curr. Opin. Rheumatol. 2003, 16(1), 67-75. |
| Apolipoprotein A1 | Coronary heart disease, atherosclerosis | Buxbaum, J. N., Curr. Opin. Rheumatol. 2003, 16(1), 67-75. |
| PrPSc | (Prion disease, sheep) | Wille, H., et al., J. Struc, Biol. 2000, 130(2-3), 323-338 |
| α-synuclein | Parkinson's, Alzheimer's | El-Agnaf, O. M. A. and Irvine, G. B., J. Struc. Biol. 2000, 130(2-3), 300-309 |
| Cystatin C | Cerebral hemorrhage | Sipe, J. D., Ann. Rev. Biochem. 1992, 61, 947-975 |

Methods

Compounds that may be used in the methods of the present invention include compounds found to bind to A-beta fibrils that prevent other cellular components from binding to the fibrils. Compounds that may be used in the methods of the present invention may, for example, have one or more of the following characteristics: low molecular weight, known and favorable pharmacokinetic properties, and known permeability across the blood-brain barrier.

Compounds that may be used in the methods of the present invention may include, for example, compounds of the present invention, including, for example, those listed in the embodiments presented herein.

Figure 4:
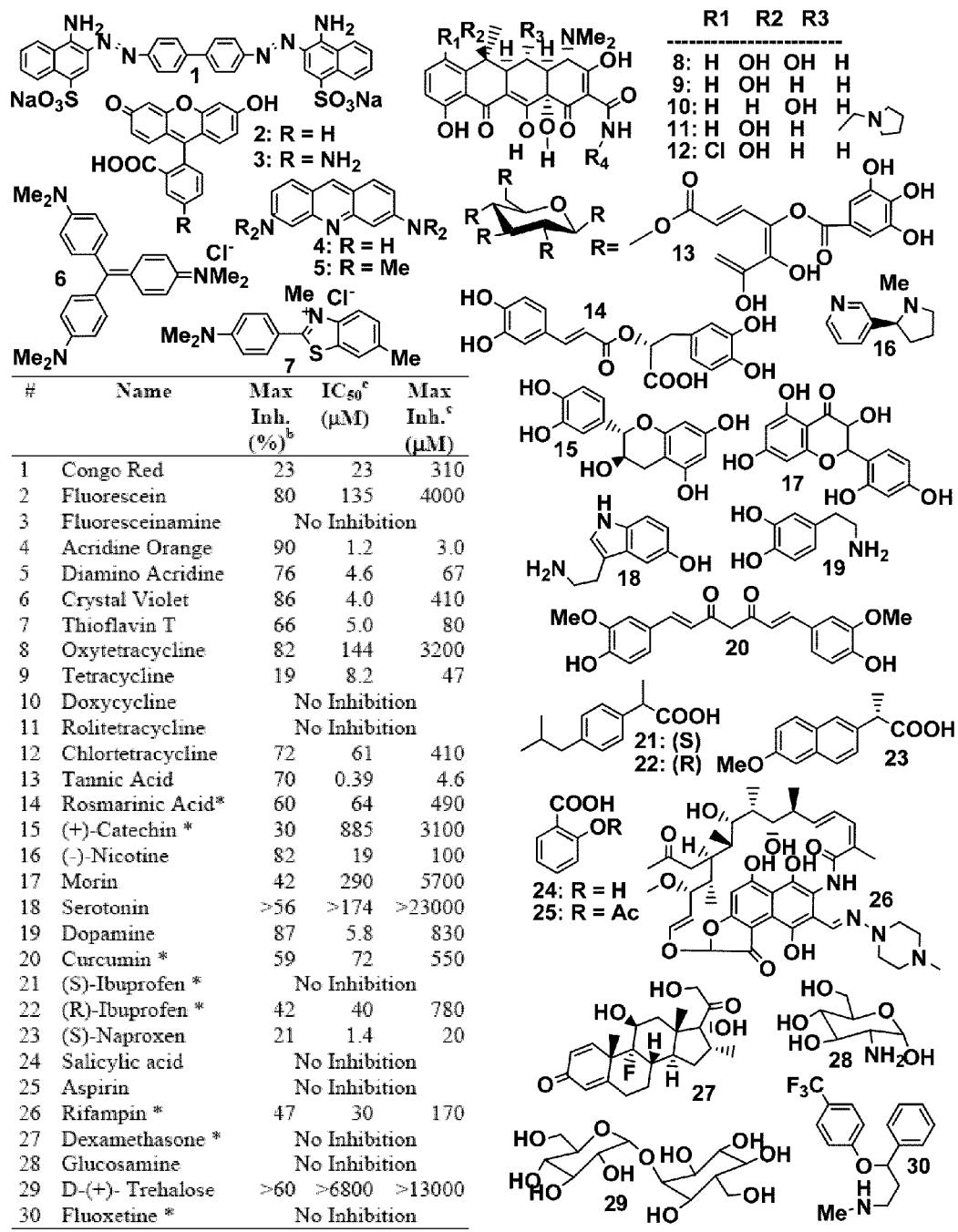
FIG. 4. Compounds used, and results from, a high throughput assay for the inhibition of IgG-A-beta interactions. Compounds are indicated by number and name. IC$_{50}$s listed give an estimate of the concentration range of the compounds required for binding to fibrils, as well as the affinity of molecules to A-beta fibrils relative to each other. Max inhibition (Max Ink) gives an estimate of the percentage of the surface of A-beta fibrils coated by the small molecules. Not shown in the Figure, but also demonstrating good efficacy in the assay are D-nicotine, oligoethylene derivatives and pegylated derivatives of 2-(p-aminophenyl)-6-methylbenzothiazole.

Compounds that may be used in the methods of the present invention also include, for example, Congo Red, Congo Red derivatives, ThT, and ThT derivatives. Compounds that may be used in the methods of the present invention may include, for example, compounds listed in C. A. Mathis, et al., Current Pharm. Design, 2004, 10:1469-92; and Hintersteiner, M., et al., Nature Biotechnology, 2005, 23:577-83. Compounds that may be used in the methods of the present invention may be radiolabeled, for example, for diagnostic imaging, such as that performed using single photon emission computed tomography (SPECT) or positron emission tomography (PET). In illustrative embodiments, the compounds have the ability to cross the blood brain barrier. (Di, L., et al., Curr. Opin. Chem. Bio. 2003, 7(3), 402-408; Abraham, M. H., Eur. J. Med. Chem. 2004, 39(3), 235-240; Mathis, C. A., et al., Current Pharm. Design, 2004, 10:1469-92) Compounds that may be used in the methods of the present invention include, for example, those showing inhibitory activity as presented in FIG. 4, such as, for example, compounds selected from the group consisting of Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof. Compounds that may be used in the present invention include, for example, those compounds showing a greater inhibitory activity as shown in FIG. 4, such as, for example, compounds selected from the group consisting of Fluoroscein, Acridine Orange, Diamino Acridine, Crystal Violet, Thioflavin T, Oxytetracycline, Chlortetracycline, Tannic Acid, Rosmarinic Acid, (+)-Catechin, (−)-Nicotine, Morin, Serotonin, Dopamine, Curcumin, (R)-Ibuprofen, Rifampin, D-(+)-Trehalose, D-nicotine, pegylated derivatives of 1-(p-aminophenyl)-6-methylbenzothiazole, and derivatives and analogs thereof. Compounds that may be used in the present invention include, for example, those compounds showing a greater inhibitory activity as shown in FIG. 4, such as, for example, Fluoroscein, Acridine Orange, Diamino Acridine, Crystal Violet, Thioflavin T, Oxytetracycline, Chlortetracycline, Tannic Acid, Rosmarinic Acid, (+)-Catechin, (−)-Nicotine, Serotonin, Dopamine, Curcumin, Rifampin, D-(+)-Trehalose, D-nicotine, pegylated derivatives of 1-(p-aminophenyl)-6-methylbenzothiazole, and derivatives and analogs thereof. Compounds that may be used in the present invention include, for example, those compounds showing a greater inhibitory activity as shown in FIG. 4, such as, for example, Fluoroscein, Acridine Orange, Diamino Acridine, Crystal Violet, Thioflavin T, Oxytetracycline, Chlortetracycline, Tannic Acid, Rosmarinic Acid, (+)-Catechin, (−)-Nicotine, Dopamine, D-(+)-Trehalose, and derivatives and analogs thereof. Compounds that may be used in the present invention include, for example, those compounds showing a greater inhibitory activity as shown in FIG. 4, such as, for example, Fluoroscein, Acridine Orange, Diamino Acridine, Crystal Violet, Oxytetracycline, Chlortetracycline, Tannic Acid, (+)-Catechin, (−)-Nicotine, Dopamine, and derivatives and analogs thereof. Compounds that may be used in the present invention include, for example, those compounds showing a greater inhibitory activity as shown in FIG. 4, such as, for example, Fluoroscein, Acridine Orange, Crystal Violet, Oxytetracycline, (+)-Catechin, (−)-Nicotine, Dopamine, and derivatives and analogs thereof.

In other examples of the present invention, compounds that may be used to prevent or alleviate the symptoms of a neuronal disease such as, for example, Alzheimer's disease include, for example, compounds selected from the group consisting of Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof. Compounds that may be used in the present invention include, for example, those compounds showing a greater inhibitory activity as shown in FIG. 4, such as, for example, compounds selected from the group consisting of Fluoroscein, Acridine Orange, Diamino Acridine, Crystal Violet, Thioflavin T, Oxytetracycline, Chlortetracycline, Tannic Acid, Rosmarinic Acid, (+)-Catechin, (−)-Nicotine, Morin, Serotonin, Dopamine, Curcumin, (R)-Ibuprofen, Rifampin, D-(+)-Trehalose, D-nicotine, pegylated derivatives of 1-(p-aminophenyl)-6-methylbenzothiazole, and derivatives and analogs thereof. Compounds that may be used in the present invention include, for example, those compounds showing a greater inhibitory activity as shown in FIG. 4, such as, for example, Fluoroscein, Acridine Orange, Diamino Acridine, Crystal Violet, Thioflavin T, Oxytetracycline, Chlortetracycline, Tannic Acid, Rosmarinic Acid, (+)-Catechin, (−)-Nicotine, Serotonin, Dopamine, Curcumin, Rifampin, D-(+)-Trehalose, D-nicotine, pegylated derivatives of 1-(p-aminophenyl)-6-methylbenzothiazole, and derivatives and analogs thereof. Compounds that may be used in the present invention include, for example, those compounds showing a greater inhibitory activity as shown in FIG. 4, such as, for example, Fluoroscein, Acridine Orange, Diamino Acridine, Crystal Violet, Thioflavin T, Oxytetracycline, Chlortetracycline, Tannic Acid, Rosmarinic Acid, (+)-Catechin, (−)-Nicotine, Dopamine, D-(+)-Trehalose, and derivatives and analogs thereof. Compounds that may be used in the present invention include, for example, those compounds showing a greater inhibitory activity as shown in FIG. 4, such as, for example, Fluoroscein, Acridine Orange, Diamino Acridine, Crystal Violet, Oxytetracycline, Chlortetracycline, Tannic Acid, (+)-Catechin, (−)-Nicotine, Dopamine, and derivatives and analogs thereof. Compounds that may be used in the present invention include, for example, those compounds showing a greater inhibitory activity as shown in FIG. 4, such as, for example, Fluoroscein, Acridine Orange, Crystal Violet, Oxytetracycline, (+)-Catechin, (−)-Nicotine, Dopamine, and derivatives and analogs thereof.

In other, illustrative examples of the present invention, compounds that may be used to prevent or alleviate the symptoms of a neuronal disease such as, for example, Alzheimer's disease include, for example, compounds selected from the group consisting of Fluoroscein, Diamino Acridine, Crystal Violet, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof. Compounds that may be used include, for example, those compounds showing a greater inhibitory activity as shown in FIG. 4, such as, for example, compounds selected from the group consisting of Fluoroscein, Diamino Acridine, Crystal Violet, Oxytetracycline, Chlortetracycline, Tannic Acid, Rosmarinic Acid, (+)-Catechin, (−)-Nicotine, Morin, Serotonin, Dopamine, Curcumin, (R)-Ibuprofen, Rifampin, D-(+)-Trehalose, D-nicotine, pegylated derivatives of 1-(p-aminophenyl)-6-methylbenzothiazole, and derivatives and analogs thereof. Compounds that may be used include, for example, those compounds showing a greater inhibitory activity as shown in FIG. 4, such as, for example, Fluoroscein, Diamino Acridine, Crystal Violet, Oxytetracycline, Chlortetracycline, Tannic Acid, Rosmarinic Acid, (+)-Catechin, (−)-Nicotine, Serotonin, Dopamine, Curcumin, Rifampin, D-(+)-Trehalose, pegylated derivatives of 1-(p-aminophenyl)-6-methylbenzothiazole, and derivatives and analogs thereof. Compounds that may be used include, for example, those compounds showing a greater inhibitory activity as shown in FIG. 4, such as, for example, Fluoroscein, Diamino Acridine, Crystal Violet, Oxytetracycline, Chlortetracycline, Tannic Acid, Rosmarinic Acid, (+)-Catechin, (−)-Nicotine, Dopamine, D-(+)-Trehalose, and derivatives and analogs thereof. Compounds that may be used include, for example, Fluoroscein, Crystal Violet, Oxytetracycline, Chlortetracycline, Tannic Acid, Rosmarinic Acid, (+)-Catechin, (−)-Nicotine, Dopamine, D-(+)-Trehalose, and derivatives and analogs thereof. Compounds that may be used include, for example, those compounds showing a greater inhibitory activity as shown in FIG. 4, such as, for example, Fluoroscein, Diamino Acridine, Crystal Violet, Oxytetracycline, Chlortetracycline, Tannic Acid, (+)-Catechin, (−)-Nicotine, Dopamine, and derivatives and analogs thereof. Compounds that may be used include, for example, Fluoroscein, Crystal Violet, Oxytetracycline, Chlortetracycline, Tannic Acid, (+)-Catechin, (−)-Nicotine, Dopamine, and derivatives and analogs thereof. Compounds that may be used include, for example, those compounds showing a greater inhibitory activity as shown in FIG. 4, such as, for example, Fluoroscein, Crystal Violet, Oxytetracycline, (+)-Catechin, (−)-Nicotine, Dopamine, and derivatives and analogs thereof.

In yet other, illustrative examples of the present invention, compounds that may be used for diagnostic imaging of A-beta fibrils include, for example, compounds selected from the group consisting of Fluoroscein, Diamino Acridine, Crystal Violet, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof. Compounds that may be used include, for example, those compounds showing a greater inhibitory activity as shown in FIG. 4, such as, for example, compounds selected from the group consisting of Fluoroscein, Diamino Acridine, Crystal Violet, Oxytetracycline, Chlortetracycline, Tannic Acid, Rosmarinic Acid, (+)-Catechin, (−)-Nicotine, Morin, Serotonin, Dopamine, Curcumin, (R)-Ibuprofen, Rifampin, D-(+)-Trehalose, D-nicotine, pegylated derivatives of 1-(p-aminophenyl)-6-methylbenzothiazole, and derivatives and analogs thereof. Compounds that may be used include, for example, those compounds showing a greater inhibitory activity as shown in FIG. 4, such as, for example, Fluoroscein, Diamino Acridine, Crystal Violet, Oxytetracycline, Chlortetracycline, Tannic Acid, Rosmarinic Acid, (+)-Catechin, (−)-Nicotine, Serotonin, Dopamine, Curcumin, Rifampin, D-(+)-Trehalose, D-nicotine, pegylated derivatives of 1-(p-aminophenyl)-6-methylbenzothiazole, and derivatives and analogs thereof. Compounds that may be used include, for example, those compounds showing a greater inhibitory activity as shown in FIG. 4, such as, for example, Fluoroscein, Diamino Acridine, Crystal Violet, Oxytetracycline, Chlortetracycline, Tannic Acid, Rosmarinic Acid, (+)-Catechin, (−)-Nicotine, Dopamine, D-(+)-Trehalose, and derivatives and analogs thereof. Compounds that may be used include, for example, Fluoroscein, Crystal Violet, Oxytetracycline, Chlortetracycline, Tannic Acid, Rosmarinic Acid, (+)-Catechin, (−)-Nicotine, Dopamine, D-(+)-Trehalose, and derivatives and analogs thereof. Compounds that may be used include, for example, those compounds showing a greater inhibitory activity as shown in FIG. 4, such as, for example, Fluoroscein, Diamino Acridine, Crystal Violet, Oxytetracycline, Chlortetracycline, Tannic Acid, (+)-Catechin, (−)-Nicotine, Dopamine, and derivatives and analogs thereof. Compounds that may be used include, for example, Fluoroscein, Crystal Violet, Oxytetracycline, Chlortetracycline, Tannic Acid, (+)-Catechin, (−)-Nicotine, Dopamine, and derivatives and analogs thereof. Compounds that may be used include, for example, Fluoroscein, Crystal Violet, Oxytetracycline, Chlortetracycline, Tannic Acid, (+)-Catechin, (−)-Nicotine, Dopamine, and derivatives and analogs thereof. Compounds that may be used include, for example, those compounds showing a greater inhibitory activity as shown in FIG. 4, such as, for example, Fluoroscein, Crystal Violet, Oxytetracycline, (+)-Catechin, (−)-Nicotine, Dopamine, and derivatives and analogs thereof.

Compounds

Compounds of the present invention include, for example, those of Formula I, including those listed as embodiments, exemplary embodiments, and examples, thereof. For example, compounds include compounds such as BTA-EG$_4$, BTA-EG$_6$, BTA-AZA-Crown$_5$, or BTA-EG$_6$-BTA.

The terms "halo" or "halogen," by themselves or as part of another substituent, mean, unless otherwise stated, a fluorine, chlorine, bromine, or iodine atom.

The compounds of the present invention, and compounds used in the methods of the present invention, may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention and compounds used in the methods of the present invention, contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention and compounds used in the methods of the present invention, contain both basic and acidic functionalities that allow the compounds to be converted into either base or acid addition salts.

Certain compounds of the present invention, and compounds used in the methods of the present invention, can exist in unsolvated forms as well as solvated forms, including hydrated forms. In general, the solvated forms are equivalent to unsolvated forms and are encompassed within the scope of the present invention. Certain compounds of the present invention and compounds used in the methods of the present invention, may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)-for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention and compounds used in the methods of the present invention, may also contain unnatural proportions of atomic isotopes at one or more of atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, and compounds used in the methods of the present invention, whether radioactive or not, are encompassed within the scope of the present invention.

The compounds of the present invention may be synthesized using one or more protecting groups generally known in the art of chemical synthesis. The term "protecting group" refers to chemical moieties that block some or all reactive moieties of a compound and prevent such moieties from participating in chemical reactions until the protective group is removed, for example, those moieties listed and described in Greene, et al., Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

The term "pharmaceutically acceptable salts" is meant to include salts of active compounds which are prepared with relatively nontoxic acids or bases, depending on the particular substituent moieties found on the compounds described herein. When compounds of the present invention and compounds used in the methods of the present invention, contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention and compounds used in the methods of the present invention, contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions.

Assays

Provided herein in the Examples are examples of screening assays that utilize 96 well microtiter plates. It will be apparent to those of ordinary skill in the art that these assays may be adapted for other types of microtiter plates, including those made of various materials and comprising various numbers of wells. Further, it is apparent to those of ordinary skill in the art that these assays may be adapted to other high throughput methods, including other solid supports methods such as beads, microarrays, and stamping. (Mayer, M., et al., Proteomics, 2004, 4:2366-76; G. MacBeath and S. L. Schreiber, Science, 2000 289(5485): 1760-1763.)

The A-beta fibrils, A-beta fibrils pre-incubated with a test compound, or the detection reagent may, for example, be immobilized to a solid support. It is understood that immobilization can occur by any means, including for example; by covalent attachment, by electrostatic immobilization, by attachment through a ligand/ligand interaction, by contact or by depositing on the surface.

As used herein "solid support" or "solid carrier" means any solid phase material upon which an oligomer is synthesized, attached, ligated or otherwise immobilized. Solid support encompasses terms such as "resin", "solid phase", "surface" and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, a gel, or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

Microarray or array means a predetermined spatial arrangement of samples present on a solid support or in an arrangement of vessels. These samples may be, for example, A-beta fibrils, A-beta fibrils pre-incubated with test compounds, or may, for example, be second binding molecules or detection antibodies where, for example, the solid support is bound to the detection reagent, and the assay comprises adding the preincubated A-beta fibrils to the second binding molecule. Certain array formats are referred to as a "chip" or "biochip" (M. Schena, Ed. Microarray Biochip Technology, BioTechnique Books, Eaton Publishing, Natick, Mass. (2000). An array can comprise a low-density number of addressable locations, e.g. 2 to about 12, medium-density, e.g. about a hundred or more locations, or a high-density number, e.g. a thousand or more. Typically, the array format is a geometrically regular shape that allows for fabrication, handling, placement, stacking, reagent introduction, detection, and/or storage. The array may be configured in a row and column format, with regular spacing between each location. Alternatively, the locations may be bundled, mixed or homogeneously blended for equalized treatment or sampling. An array may comprise a plurality of addressable locations configured so that each location is spatially addressable for high-throughput handling, robotic delivery, masking, or sampling of reagents, or by detection means including scanning by laser illumination and confocal or deflective light gathering.

The presence of a compound that blocks the binding of a second binding molecule to A-beta fibrils is generally detected using a second binding molecule that binds to A-beta fibrils. The second binding molecule is either directly labeled, i.e., comprise or reacts to produce a detectable label, or is indirectly labeled, i.e., bind to a molecule comprising or reacting to produce a detectable label. Labels can be directly attached to or incorporated into the detection reagent by chemical or recombinant methods.

In one embodiment, the detection reagent, the molecule that is detected in the screening assay, is a second binding molecule that is an antibody that specifically binds to A-beta peptide. In another embodiment, the detection reagent is an antibody that specifically binds to the second binding molecule. In one embodiment, a label is coupled to the detection reagent through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. Preferred linkers are often flexible amino acid subsequences which are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels used in the assays of the present invention, which are attached to the detection reagent, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

For use of the present invention in the clinic, preferred labels are non-radioactive and readily detected without the necessity of sophisticated instrumentation. Preferably, detection of the labels will yield a visible signal that is immediately discernable upon visual inspection. One preferred example of detectable secondary labeling strategies uses an antibody that recognizes A-beta amyloid fibrils in which the antibody is linked to an enzyme (typically by recombinant or covalent chemical bonding). The antibody is detected when the enzyme reacts with its substrate, producing a detectable product. Preferred enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer, and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Research Reagents

The present invention is further directed to research reagents used to detect amyloid proteins and amyloid plaques. Such research reagents are compounds that bind to amyloid proteins, including, for example, but not limited to, the compounds of the present invention. Research reagents of the present invention may further comprise dyes or other detectable labels. Thus, research reagents of the present invention include, for example, compositions that comprise the compounds of the present invention, and compounds of the present invention.

The research reagents may be used, for example, to detect the presence of amyloid plaques in vivo, in tissues, in cells, and in tissue or cell extracts. The research reagents may be used, for example, to determine the existence of an amyloid-associated disease, or to assist in screening for compounds that may prevent or alleviate the symptoms of the disease. The research reagents may be used, for example, to inhibit the interaction of an amyloid protein with a second binding protein, thus enabling the study of a cellular or disease mechanism. In one exemplary embodiment, a method is provided for detecting the presence of an amyloid protein, or an amyloid plaque, comprising contacting said amyloid protein or amyloid plaque with a research reagent of the present invention, and detecting binding of the research reagent to the amyloid protein or amyloid plaque.

Kits

The present invention is also directed to kits that utilize the screening assays described herein. A basic kit for measuring the presence and/or activity of an A-beta fibril binding molecule includes a vessel or surface on which A-beta fibril molecules can bind, A-beta fibril molecules, and an anti-A-beta antibody. Reagents used to detect the binding of the anti-A-beta antibody, such as reagents used for ELISA assays may also be included in the kit. The kit may also comprise instructions for use of the kit. Rather than including an anti-A-beta antibody, the kit may include other detectable molecules that are known to bind A-beta fibril molecules. The kit may also include an appropriate amount of reaction buffer disposed in a suitable container.

"Instructions for use," is a tangible expression describing the reagent concentration or at least one assay method parameter such as the relative amount of reagent and sample to be admixed, maintenance time periods for reagent/sample admixtures, temperature, buffer conditions, and the like. The instructions for use are suitable to enable an analyst to carry out the desired assay.

In some embodiments, the kits can include a container containing A-beta fibrils, either free or bound to solid supports. Also included in the kits can be a suitable membrane, solid support, or vessel used in conducting the assay such as, for example, a microtiter plate, for example, but not limited to, a polystyrene plate. Preferably, the kits will also include reagents used in the described assays, including reagents useful for detecting the binding of a compound to the fibrils, such as, for example, a detectable molecule that binds to A-beta fibrils. For example, the kits may include an anti-A-beta antibody. The antibody itself may have a label, such as a flourescein label or dye, that may allow it to be detected. Other materials useful in the performance of the assays can also be included in the kits, including test tubes, transfer pipettes, and the like. The kits can also include written instructions for the use of one or more of these reagents in any of the assays described herein.

The kits of the invention can also include an internal and/or an external control. The control can consist of, for example, Congo Red, a Congo Red derivative, ThT or a ThT derivative. The control may, for example, be selected from the group consisting of, Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and derivatives and analogs thereof. The kits of the present invention can contain materials sufficient for one assay, or can contain sufficient materials for multiple assays.

Also included in the scope of the present invention are kits that may be used to detect amyloid proteins or amyloid plaques, wherein such kits comprise research reagents of the present invention. A basic kit for detecting or measuring the quantity of amyloid protein or an amyloid plaque includes at least one research reagent of the present invention. Reagents used to detect the binding of the research reagent, such as dyes, labels, antibodies, and the like, may also be included in the kit. The kit may also comprise instructions for use of the kit. The kit may also include an appropriate amount of reaction buffer disposed in a suitable container.

"Instructions for use," is a tangible expression describing the reagent concentration or at least one assay method parameter such as the relative amount of reagent and sample to be admixed, maintenance time periods for reagent/sample admixtures, temperature, buffer conditions, and the like. The instructions for use are suitable to enable an analyst to carry out the desired assay.

In some embodiments, the kits can include a container containing A-beta fibrils, either free or bound to solid supports, as a positive control. Or, the kits may include a container containing amyloid plaques as a positive control. Also included in the kits can be a suitable membrane, solid support, or vessel used in conducting the assay such as, for example, a microtiter plate, for example, but not limited to, a polystyrene plate. Preferably, the kits will also include reagents used in the described assays, including reagents useful for detecting the binding of a research reagent to the fibrils, such as, for example, a detectable molecule that binds to research reagent/A-beta fibril complexes. Other materials useful in the performance of the assays can also be included in the kits, including test tubes, transfer pipettes, and the like. The kits can also include written instructions for the use of one or more of these reagents in any of the assays described herein.

The amounts of the various reagents in the kits can be varied depending on various factors, such as the optimum sensitivity of the assay, the number of assays to be performed, etc.

It is within the scope of the invention to provide manual test kits or test kits for use in automated analyzers.

Formulation

While the compounds of the present invention will typically be used in therapy for human patients, they may also be used in veterinary medicine to treat similar or identical diseases. The compounds of the present invention and compounds used in the methods of the present invention, include geometric and optical isomers.

The compounds according to the invention are effective over a wide dosage range. For example, in the treatment of adult humans, dosages from 0.01 to 1000 mg, from 0.02 to 800 mg, from 0.05 to 700 mg, from 0.1 to 650 mg, from 0.2 to 600 mg, from 0.5 to 500 mg, from 0.5 to 300 mg, from 0.5 to 250 mg, 0.5 to 100 mg, from 1 to 100 mg, from 1 to 50 mg, and from 1 to 50 mg per day, from 5 to 40 mg per day are examples of dosages that may be used. One example of a dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20 th ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

In therapeutic and/or diagnostic applications, the compounds of the invention may be formulated for a variety of modes of administration, including systemic and topical or localized administration. Techniques and formulations generally may be found in Remington: The Science and Practice of Pharmacy (20th ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20th ed.) Lippincott, Williams & Wilkins (2000). Suitable routes may include oral, buccal, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intraperitoneal, intranasal, or intraocular injections.

In illustrative embodiments, for injection, such as, for example, intravenous delivery, the agents of the invention may be formulated in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration, or for targeted administration, such as that targeted to the brain, is within the scope of the invention. With proper choice of carrier and suitable manufacturing practice, the compositions of the present invention, in particular, those formulated as solutions, may be administered parenterally, such as by intravenous injection. The compounds may be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising one or more buffers, excipients, salts, preservative, auxiliaries and the like which facilitate processing of the active compounds into preparations which may be used pharmaceutically. The preparations formulated for oral administration may be in the form of tablets, dragees, capsules, or solutions. Appropriate pharmaceutically acceptable carriers are known to those of ordinary skill in the art and may be found in, for example, Remington: The Science and Practice of Pharmacy (20th ed.) Lippincott, Williams & Wilkins (2000).

Pharmaceutical preparations for oral use may be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that may be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Pharmaceutical compositions of the present invention are those that, in addition to specifically binding amyloid in vivo and capable of crossing the blood brain barrier, are also nontoxic at appropriate dosage levels and have a satisfactory duration of effect.

EXAMPLES

All synthetic reagents were from Aldrich, Fisher Scientific, Alfa Aesar or Fluka, and were used as received. Water was filtered through a NANOPure Diamond™ water purification system from Barnstead (18.2 μΩ/cm). Aβ-peptide (1-42) was obtained from Biopeptide Co, LLC, San Diego, Calif.; 96-well plates from Nalge Nunc International, Rochester, N.Y.; catalase from human erythrocytes (Lot #B67459) from Calbiochem, San Diego, Calif.; IgGs from Abcam, Cambridge, Mass.; and bovine serum albumin (BSA, fraction V) from Omni Pur.

NMR spectra were obtained on a Varian 400 MHz spectrometer. Chemical shifts are reported in ppm relative to residual solvent. FT-IR spectra were obtained on a Nicholet MAGNA-IR 440 spectrometer. A Perkin Elmer HTS-7000 Bio Assay reader was used to measure the absorbance of, the assays. UV-Vis absorbencies were determined with a Beckman-Coulter DU500 spectrometer.

Example 1

A-beta fibrils were grown in vitro from synthetic AD-related A-beta peptides (residues 1-42). Fibrils were characterized by atomic force microscopy. Images indicated the presence of fibrils that were consistent with literature reports (Hilbich, C., et al., J. Mol. Biol. 1992, 228: 460.) in terms of size (5-10 nm in diameter and >400 nm long) and in terms of morphology (single fibrils and bundles of fibrils). The wells of commercial 96-well plates were coated with freshly prepared A-beta fibrils and the fibrils were incubated with solutions of ThT. After removal of excess ThT, the ThT-coated fibrils in the wells were treated with a monoclonal anti-A-beta IgG (clone 6E10, derived from residues 3-8 of A-beta peptide as antigens). The interaction of the anti-A-beta IgG with the ThT-coated A-beta fibrils was quantified using an ELISA-based assay.

FIG. 2*a* shows that ThT had an inhibition concentration corresponding to 50 percent inhibition ($IC_{50}$) of 5 μM for the binding of the anti-A-beta IgG (clone 6E10, 0.16 μg $mL^{-1}$) to the A-beta fibrils (deposited from solutions containing 1.3 μM A-beta peptide). Because the final concentration of the A-beta fibrils deposited in the wells was not determined, the A-beta fibrils (1.3 μM) were also incubated with solutions of ThT prior to depositing the coated fibers into the wells and an $IC_{50}$ of 60 μM was measured (See Example 3, FIG. 3). For comparison, an $IC_{50}$ of ~1 μM was observed when a 0.3 μM solution of A-beta peptide was used in the control procedure (data not shown). Therefore, it would be expected that observed $IC_{50}$'s would be different using the two procedures. A total inhibition of 65% of the interaction between this IgG and A-beta fibrils was measured when the fibrils were incubated with a 50 μM solution of ThT. 0 percent inhibition was defined as the UV-Vis signal observed when the assay is run in the absence of ThT and 100 percent inhibition was defined as the UV-Vis signal observed when the assay is run in the absence of both amyloid fibril and ThT. Solutions of ThT with concentrations higher than 50 μM did not increase the total inhibition of the IgG-A-beta fibril interactions above 65%. Coating the fibrils in solutions of ThT (>100 μM of Tyr) prior to deposition into wells resulted in a maximum inhibition of ~80% of the protein-amyloid interactions (See Example 3, FIG. 3). Exposing the ThT-coated A-beta fibrils to prolonged washing steps (from 0-4 hrs) with PBS buffer prior to incubation with primary anti-A-beta IgG did not affect the total amount of inhibition of the IgG-amyloid interactions, suggesting the rate of unbinding of ThT from the A-beta fibrils is slow relative to the timescale of the binding assay.

Example 2

To demonstrate that this surface-coatings approach can extend to other proteins that bind to A-beta fibrils, the ability of ThT to inhibit the interaction of A-beta fibrils with an anti-A-beta IgG raised against a different epitope of A-beta peptide (clone AMY-33, derived from residues 1-28 of A-beta peptide as antigens) was tested. An $IC_{50}$ of 0.4 μM (FIG. 2*b*) for ThT with this IgG (clone AMY-33) was measured under the same conditions used to assay the first anti-A-beta IgG (clone 6E10). A maximum inhibition of ~65% of this IgG (clone MY-33)-A-beta fibril interaction was measured with solutions of ThT having concentrations of 10 μM or higher. No inhibition of the interaction between the IgGs and A-beta fibrils in control experiments using l-naphthol-4-sulfonate (FIG. 2c) were observed. Structurally-similar molecules to 1-naphthol-4-sulfonate do not interact with A-beta fibrils. (Villa, S., et al., Farmaco 2003, 58: 929.) This may suggest that binding of the small molecule to the A-beta fibrils is necessary for the observed inhibition with ThT.

Without limitation as to the possible mechanism of action of inhibition, the observed partial inhibition of the IgG-amyloid interactions by ThT may be, for example, due to ThT not binding (or binding differently) to the terminal ends of the A-beta fibrils (ThT is known to bind only to the fibril form of A-beta peptides (LeVine III, H. Arch. Biochem. Biophys. 1997, 342: 306)). It is possible, therefore, that about 35% of the surface area of each A-beta fibril (presumably localized near the ends of A-beta fibril) may still be accessible for binding by anti-A-beta IgGs even after coating the surface of A-beta fibrils with ThT. Perhaps molecules that more thoroughly coat the surface of A-beta fibrils compared to ThT may show increased inhibition of protein-A-beta fibril interactions.

These examples demonstrate that ThT can inhibit 65±10% of IgG-A-beta fibril interactions. The generation of protein-resistive surface coatings on amyloid fibrils with small molecules may lead to new therapeutic strategies for the inhibition of harmful protein-amyloid interactions in neurodegenerative diseases.

Additional References

Yan, S. D. et al. Nature 1997, 389, 689: Yan, S. D.; Fu, J.; Sot, C.; Chen, X.; Zhu, H.; Al-Mohanna, F.; Collison, K.; Zhu, A.; Stem, E.; Saido, T.; Tohyama, M.; Ogawa, S.; Roher, A.; Stern, D. Nature 1997, 389, 689:

Yan, S. D. et al. J. Biol. Chem. 1999, 274, 2145: Yan, S. D.; Shi, Y.; Zhu, A.; Fu, J.; Zhu, H.; Zhu, Y.; Gibson, L; Stem, E.; Collison, K.; Al-Mohanna, F.; Ogawa, S.; Roher, A.; Clarke, S. G.; Stem, D. M. J. Biol. Chem. 1999, 274, 2145.

Lustbader, J. W. et al. Science 2004, 304, 448: Lustbader, J. W.; Girilli, M.; Lin, C.; Xu, H. W.; Takuma, K.; Wang, N.; Caspersen, C.; Chen, X.; Pollak, S.; Chaney, M.; Trinchese, F.; Liu, S.; Gunn-Moore, F.; Lue, L. F.; Walker, D. G.; Kuppusamy, P:; Zewier, Z. L.; Aranchio, O.; Stem, D.; Yan, S. S. D.; Wu, H. Science 2004, 304, 448.

Yan, S. D. et al. Nature 1996, 382, 685: Yan, S. D.; Chen, X.; Fu, J.; Chen, M.; Zhu, H.; Roher, A.; Slattery, T.; Zhao, L.; Nagashima, M.; Morser, J.; Migheli, A.; Nawroth, P.; Stem, D.; Schmidt, A. M. Nature 1996, 382, 685.

Example 3

Assay Methods

A-beta fibrils were grown from synthetic A-beta (142) peptides (Biopeptide Co, LLC, San Diego, Calif., USA) by dissolving 30 μg of peptide in 90 μL of water and incubating at 37° C. for 72 hours. Fibrils were characterized by atomic force microscopy. Images indicated the presence of fibrils (FIG. 1a) that were consistent with literature reports in terms of size (5-10 nm in diameter and >400 nm long) and in terms of morphology (single fibrils and bundles of fibrils).

The wells of commercial 96-well plates were coated with freshly prepared A-beta fibrils. Each well of a 96 well plate (Titertek®, Huntsville, Ala., USA) was coated for 12 hours with 50 μL of a 5.8 μg/mL (1.3 μM) solution of A-beta peptides (present in fibril form) in phosphate buffered saline (PBS, 10 mM $NaH_2PO_4/Na_2HPO_4$, 138 mM NaCl, 2.7 mM KCl, pH=7.4). After removal of the excess sample, 50 μl, of thioflavin T or 1-naphthol-4-sulfonate solutions in PBS buffer (various concentrations were obtained by diluting a stock solution with PBS buffer) were incubated in the wells for 1.5 or 12 hours, followed by removal of the excess solutions. Alternatively, amyloid fibrils were preincubated for 1.5 hours with ThT at various concentrations by adding amyloid fibrils (having a final concentration of 1.3 μg/mL or 5.8 μg/mL) to the ThT solutions. Wells were coated with ThT-bound fibrils by addition of 50 μL of the preincubated solutions per well and incubation for 1.5 hours. Excess solutions were then discarded. To test if the bound Thioflavin T will be removed during the process of the assay, we subjected the sample to extensive washing steps: 300 μL of PBS was added to the wells and equilibrated for 15 minutes, removed, and then repeated as many as 16 times. The following steps were identical for both methods: All wells were blocked for 30 minutes by adding 300 μL of a 1 (w/v) % solution of bovine serum albumin (BSA, Fraction V, OmniPur) in PBS buffer. Wells were washed once with 300 μL of PBS buffer and incubated for an additional 1 hour with 50 μL of a 0.16 μg/mL or 0.5 μg/mL of anti-A-beta IgG (dilution 1:6000 in BSA/PBS for clone 6E10 or dilution 1:1000 in 1% BSA/PBS for clone AMY-33, respectively). The wells were washed twice with 300 μL PBS buffer and incubated for 45 minutes with 50 μL of the secondary IgG (1 μg/mL, dilution 1:1000 in 1% BSA/PBS), and washed twice with 300 μL PBS buffer. Bound secondary IgGs were detected by the addition of 50 μL of a p-nitrophenyl phosphate solution (1 mg/mL in 0.1M diethanol amine/0.5 mM magnesium chloride). After the desired intensities were achieved, the enzymatic reaction was quenched after 0.5-2 hours by the addition of 50 μL of a 0.25N sodium hydroxide solution. Absorbance intensities were determined at 405 nm using a UV-Vis spectroscopic plate reader (HTS 7000 Bio Assay Reader, Perkin Elmer, Fremont, Calif., USA). Each run was performed five times and averaged. Graphs were plotted and fitted with the sigmoidal curve fitting option in Origin 6.0 (Microcal Software, Inc., Northhampton, Mass., USA).

Sodium chloride and sodium dihydrogen phosphate hydrate were purchased from Fisher Scientific. Potassium chloride and sodium hydroxide were purchased from Baker. Magnesium chloride was purchased from Sigma. Diethanolamine, p-nitrophenyl phosphate, and 1-naphthol-4-sulfonic acid (sodium salt) were purchased from Fluka. Thioflavin T (ThT) was purchased from MP Biomedica. All reagents were used without further purification. Water (18.2 μΩ/cm) was filtered through a NANOPure Diamond™ (Barnstead) water purification system before use. Metrology Probe™, Tap 300 (Ted Pella, Inc, Redding, Calif., USA) probe tips were used for AFM measurements.

As primary IgGs against A-beta, monoclonal anti-A-beta IgG (clone 6E10, mouse, derived from residues 3-8 of A-beta peptide as antigens,) was obtained from Abeam, Cambridge, Mass., (Lot # 79040) and anti-A-beta IgG (clone AMY-33, mouse, derived from residues 1-28 of A-beta peptide as antigens,) was purchased from Zymed Laboratories Inc, South San Francisco, Calif., (Lot # 40487378). The secondary anti-mouse IgG (anti-mouse IgG H+L conjugated with alkaline phosphatase, polyclonal, from rabbit) was purchased from Abeam, Cambridge, Mass., (Lot # 71496 or #95504). All ELISA based procedures were done at 25° C. unless otherwise stated.

For imaging of A-beta fibrils by atomic force microscopy, 10 μL of an A-beta solution in distilled water (0.33 mg/mL) was placed on freshly cleaved mica (SPI, Westchester, Pa., USA) for 2 minutes. The solution was wicked off with filter paper and the sample was washed twice with 10 µL of water. The sample was then dried under vacuum and imaged using a DI Nanoscope-IV Multimode AFM (Veeco, Santa Barbara, Calif., USA) in tapping mode under ambient conditions.

Example 4

Compound Assays

The compounds shown in FIG. 4 were assayed using the A-beta fibril assay of Example 3 as follows.

A-beta fibrils were grown from synthetic A-beta (1-42) peptides (Biopeptide Co, LLC, San Diego, Calif., USA) by dissolving 30 µg of peptide in 90 µL of water and incubating at 37° C. for 72 hours. Fibrils were characterized by atomic force microscopy. Images indicated the presence of fibrils (FIG. 1a) that were consistent with literature reports in terms of size (5-10 nm in diameter and >400 nm long) and in terms of morphology (single fibrils and bundles of fibrils).

The wells of commercial 96-well plates were coated with freshly prepared A-beta fibrils. Each well of a 96 well plate (Nalge Nunc, Rochester, N.Y.) was coated for 2 hours with 50 µL of a 5.8 µg/mL (1.3 µM) solution of A-beta peptides (present in fibril form) in phosphate buffered saline (PBS, 10 mM $NaH_2PO_4/Na_2HPO_4$, 138 mM NaCl, 2.7 mM KCl, pH=7.4). After removal of the excess sample, 50 µL of inhibitor solutions in PBS or 5% DMSO in PBS buffer (various concentrations were obtained by diluting a stock solution with PBS buffer or the DMSO/PBS buffer solution; the DMSO was added to assist in the solubility of inhibitors that were insoluble in PBS buffer) were incubated in the wells for 12 hours, followed by removal of the excess solutions. AU wells were blocked for 30 minutes by adding 300 µL of a 1 (w/v) % solution of bovine serum albumin (BSA, Fraction V, OmniPur) in PBS buffer. Wells were washed once with 300 µL of PBS buffer and incubated for an additional 1 hour with 50 µL of a 0.16 µg/mL or 0.5 µg/mL of anti-A-beta IgG (dilution 1:6000 in BSA/PBS for clone 6E10). The wells were washed twice with 300 µL PBS buffer and incubated for 45 minutes with 50 µL of the secondary IgG (1 µg/mL, dilution 1:1000 in 1% BSA/PBS), and washed twice with 300 µL PBS buffer. Bound secondary IgGs were detected by the addition of 50 µL of a p-nitrophenyl phosphate solution (1 mg/mL in 0.1M diethanol amine/0.5 mM magnesium chloride). The enzymatic reaction was quenched after 0.5-2 hours by the addition of 50 µL of a 0.25N sodium hydroxide solution. Absorbance intensities were determined at 405 nm using a UV-Vis spectroscopic plate reader (HTS 7000 Bio Assay Reader, Perkin Elmer, Fremont, Calif., USA). Each run was performed five times and averaged. Graphs were plotted and fitted with the sigmoidal curve fitting option in Origin 6.0 (Microcal Software, Inc., Northhampton, Mass., USA).

Sodium chloride and sodium dihydrogen phosphate hydrate were purchased from Fisher Scientific. Potassium chloride and sodium hydroxide were purchased from Baker. Magnesium chloride was purchased from Sigma. Diethanolamine, p-nitrophenyl phosphate was purchased from Fluka. Inhibitors were from MP Biomedical, Sigma, Aldrich, or Fluka. All reagents were used without further purification. Water (18.2 µΩ/cm) was filtered through a NANOPure Diamond™ (Barnstead) water purification system before use. Metrology Probe™, Tap 300 (Ted Pella, Inc, Redding, Calif., USA) probe tips were used for AFM measurements.

As primary IgGs against A-beta, monoclonal anti-A-beta IgG (clone 6E10, mouse, derived from residues 3-8 of A-beta peptide as antigens,) was obtained from Abcam, Cambridge, Mass., (Lot # 79040 and 116274) The secondary anti-mouse IgG (anti-mouse IgG H+L conjugated with alkaline phosphatase, polyclonal, from rabbit) was purchased from Abcam, Cambridge, Mass., (Lot #95504). All ELISA based procedures were done at 25° C.

The assay results are shown in the Table of FIG. 4, in which percent maximum inhibition, µM maximum inhibition, and $IC_{50}$s are shown. Not shown in the table, but also showing good efficacy were D-nicotine and oligoethylene glycol derivatives of 2-(p-aminophenyl)-6-methylbenzothiazole.

Example 5

Binding of THT Derivatives to A-beta Fibrils

Molecules were assayed for their ability to bind with higher density to A-beta fibrils compared to ThT, to test whether these molecules would generate more complete protein-resistive coatings on A-beta fibrils. Substituted 2-(4-aminophenyl)-benzothiazoles (commonly referred to as "benzothiazole-aniline" or BTA) have been reported as biocompatible analogues of ThT(Klunk, W. E., et al., *Life Sci.* 2001, 69(13), 1471-1484; a) C. Solbach, M. Uebele, G. Reischl, H.-J. Machulla, *Appl. Radiation Isotope* 2005, 62(4), 591-595; b) Y. Wang, W. E. Klunk, G.-F. Huang, M. L. Debnath, D. P. Holt, C. A. Mathis, *J. Mol. Neurosci.* 2002, 19(1/2), 11-16; c) W. E. Klunk, Y. Wang, G.-f. Huang, M. L. Debnath, D. P. Holt, L. Shao, R. L. Hamilton, M. D. Ikonomovic, S. T. DeKosky, C. A. Mathis, *J. Neurosci.* 2003, 23(6), 2086-2092; C. A. Mathis, Y. Wang, W. E. Klunk, *Curr. Pharm. Design* 2004, 10(13), 1469-1492), that bind to multiple sites along the A-beta fibril axis. (A. Lockhart, L. Ye, D. B. Judd, A. T. Merritt, P. N. Lowe, J. L. Morgenstern, G. Hong, A. D. Gee, J. Brown, *J. Biol. Chem.* 2005, 280(9), 7677-7684). $BTA-EG_4$ and $BTA-EG_6$ (FIG. 1b) were synthesized and tested to determine whether these uncharged derivatives of ThT could also generate protein-resistive coatings on A-beta fibrils.

Oligoethylene glycol derivatives of ThT were tested for their ability to inhibit the binding of a monoclonal anti-Aβ IgG (clone 6E10) to AD fibrils formed from residues 1-42 of synthetic A-beta peptides (FIG. 5).

BTA-$EG_4$ and BTA-$EG_6$ inhibited (0 percent inhibition was defined as the UV-Vis signal observed when the assay is run in the absence of small molecule and define 100 percent inhibition as the UV-Vis signal observed when the assay is run in the absence of both amyloid fibrils and small molecule.) 94% and 99%, respectively, of the IgG-A-beta fibril interactions, with inhibitory concentrations corresponding to 50% inhibition ($IC_{50}$'s) of ~100 μM. These results suggest that the two BTA derivatives form almost complete IgG-resistive coatings on A-beta fibrils.

Example 6

Binding Competition to A-beta Fibrils

To test whether the derivatives of BTA could also inhibit biologically relevant protein-amyloid interactions, we investigated whether BTA-$EG_4$ and BTA-$EG_6$ could compete with two natural cellular proteins—catalase and ABAD—for binding to A-beta fibrils. Catalase and ABAD were used as natural proteins in these studies due to their previously reported interaction with aggregated A-beta and their potential importance in the pathogenesis of Alzheimer's disease. (Milton, N. G. N., et al., *Neuroreport* 2001, 12(11), 2561-2566; Milton, N. G. N., et all, *Biochem. J.* 1999, 344(2), 293-296; Yan, S. D., et al., *Int. J. Exp. Path.* 2005, 86(3), 161-171; Kissinger, C. N., et al., *J. Mol. Biol.* 2004, 342(3), 943-952; Lustbader, J. W., et al., *Science* 2004, 304(5669), p 448-452). Catalase and ABAD have also been reported to bind to different residues of A-beta (i.e., at residues 25-35 for catalase (Milton, et al., Neuroreport 2001, 12:2561-2566) and residues 1-20 for ABAD (Oppermann, U. C. T., et al., *FEBS Lett.* 1999, 451(3), 238-242; Powell, A. J., et al., *J. Mol. Biol.* 2000, 303(2), 311-327). The different sites for binding of these proteins to A-beta peptides provide an opportunity to test whether the oligoethylene glycol derivatives of BTA may have potential general utility for inhibiting the interaction between A-beta fibrils and proteins that bind to completely different regions of A-beta.

Catalase is a peroxidase enzyme that catalyzes the breakdown of $H_2O_2$ in peroxisomes (Wiemer, E. A. C., et al, *J. Immunol. Methods* 1992, 151(1-2), 165-175) and the cytoplasm (R. J. Marttila, M. Roytta, H. Lorentz, U. K. Rinne, *J. Neural. Transm.* 1988, 74(2), 87-95) and plays a central role in suppressing the level of reactive oxygen species in cells. (C. D. Putnam, A. S. Arvai, Y. Bourne, J. A. Tainer, *J. Mol. Biol.* 2000, 296(1), 295-309). Catalase has been found to be associated with Alzheimer's plaques (M. A. Lovell, W. D. Ehmann, S. M. P. Butler, W. R. Markesbery, *Neurol.* 1995, 45(9), 1594-1601) and has known protective properties against A-beta-induced toxicity in neurons. (a) C. Behl, J. B. Davis, R. Lesley, D. Schubert, *Cell* 1994, 77(6), 817-827; b) Z. Zhang, R. E. Rydel, G. J. Drzewiecki, K. Fuson, S. Wright, M. Wogulis, J. E. Audia, P. C. May, P. A. Hyslop, *J. Neurochem.* 1996, 67(4), 1595-1606). Previous reports (Milton, N. G. N., et al., *Neuroreport* 2001:12:2561-2566; Milton, N. G. N., *Biochem. J.* 1999:344:293-296) indicate that the direct interaction between catalase and some aggregated form of A-beta peptides can lead to the inactivation of catalase in vitro, suggesting that catalase-amyloid interactions may potentially contribute to the cytotoxicity of A-beta in AD. The catalase was assayed to determine whether it could associate with A-beta peptides in fibrillar form and if small molecules that bind to A-beta fibrils could be used to inhibit these catalase-A-beta fibril interactions.

FIG. 6 presents results from a standard ELISA assay (P. E. Fraser, L. K. Duffy, M. B. O'Malley, J. Nguyen, H. Inouye, D. A. Kirschner, *J. Neurosci. Res.* 1991, 28(4), 474-485) indicating that catalase indeed binds to A-beta fibrils. After incubating A-beta fibrils (P. Inbar, J. Yang, *Bioorg. Med. Chem. Lett.* 2006, 16(4), 1076-1079) with a solution of catalase, ThT was found to compete with catalase for binding to A-beta fibrils with an $IC_{50}$ for ThT of 170 µM (FIG. 6b). There was a maximum total inhibition of ~50% for the catalase-A-beta fibrils interaction at concentrations of ThT of 3 mM and higher. A significantly higher maximum total inhibition (compared to ThT) was observed of 91% for BTA-$EG_4$ and 92% for BTA-$EG_6$ for the interaction of catalase with A-beta fibrils (FIGS. 6c and 6d). An $IC_{50}$ of 590 µM for BTA-$EG_4$ and 36 µM for BTA-$EG_6$ were found for the inhibition of binding of catalase to A-beta fibrils. These results indicate that BTA-$EG_4$ and BTA-$EG_6$ can form more complete protein-resistive surface coatings on A-beta fibrils compared to ThT.

Example 7

Inhibition of A-beta Fibril-ABAD Binding Interaction

To further test the generality of using small molecules to inhibit protein—beta fibril interactions, ThT and its derivatives were tested for their ability to inhibit the interaction between A-beta fibrils and the mitochondrial protein A-beta-binding alcohol dehydrogenase (ABAD). The interaction between ABAD and aggregated A-beta peptides has been shown to lead to oxidative stress in cells and, therefore, may play a potential pathogenic role in AD. (Lustbader, J. W., et al. *Science* 2004:304:448-452; J. Frackowiak, B. Mazur-Kolecka, W. Kaczmarski, D. Dickson, *Brain Res.* 2001, 907 (1-2), 44-53). Inhibition of the interaction between ABAD and aggregated A-beta using a decoy peptide appears to protect cells from oxidative stress, (Lustbader, J. W., et al. Science 2004:304:448-452) suggesting the development of methods to inhibit ABAD-amyloid interactions may be a target for therapy against AD.

A standard ELISA assay was developed to measure ABAD binding to A-beta fibrils (FIG. 7a). ThT, BTA-$EG_4$, and BTA-$EG_6$ were then examined for their ability to inhibit the ABAD-A-beta fibril interactions. FIGS. 7b-7d demonstrate that ThT and the BTA derivatives are all able to at least partially inhibit the ABAD-A-beta fibril interactions ($IC_{50}$'s in the range of 100-500 µM). Both BTA-$EG_4$ and BTA-$EG_6$ were more effective at competitive replacement of ABAD on the A-beta fibrils compared to ThT. A ~75% total inhibition of the protein-amyloid interactions at concentrations of BTA derivatives above 4 mM compared to ~56% total inhibition of the ABAD-A-beta fibril interaction with ThT at similar concentrations was observed.

An interesting observation was that BTA-$EG_4$ and BTA-$EG_6$ inhibited catalase-A-beta fibril interactions more effectively than ABAD-A-beta fibril interactions. This observation may be due to the fact that catalase has been reported to interact with residues 25-35 of A-beta peptides, (Milton, N. G. N., et al., *Neuroreport* 2001: 12:2561-2566; Milton, N. G. N., *Biochem. J.* 1999: 344:293-296) which are within the -beta-sheet region of A-beta fibrils. (L. Li, T. A. Darden, L. Bartolotti, D. Kominos, L. G. Pedersen, Biophys. J. 1999, 76(6), 2871-2878). Since ThT and BTA derivatives are believed to associate with the -beta-sheet region of amyloid fibrils, (Lockhart, A., et al., *J. Biol. Chem.* 2005:280:7677-7684) it seems reasonable that these small molecules could effectively compete with proteins that bind in the same region along the fibrillar axis. ABAD, however, has been reported to bind to a more solvent exposed portion of A-beta (i.e., residues 1-20) (Powell, A. J., et al., *J. Mol. Biol.* 2000:303:311-327) than catalase and may not be as susceptible to ThT and its derivatives for competition for binding to A-beta fibrils. A significant difference was not observed between BTA-$EG_4$ and BTA-$EG_6$ for inhibition of the catalase-amyloid or ABAD-amyloid binding interactions. This observation suggests the BTA component of the small molecules plays the more structurally significant role compared to the small differences in the size of the oligoethylene glycol chain for inhibiting the binding of these natural proteins to A-beta fibrils.

Figure 5:
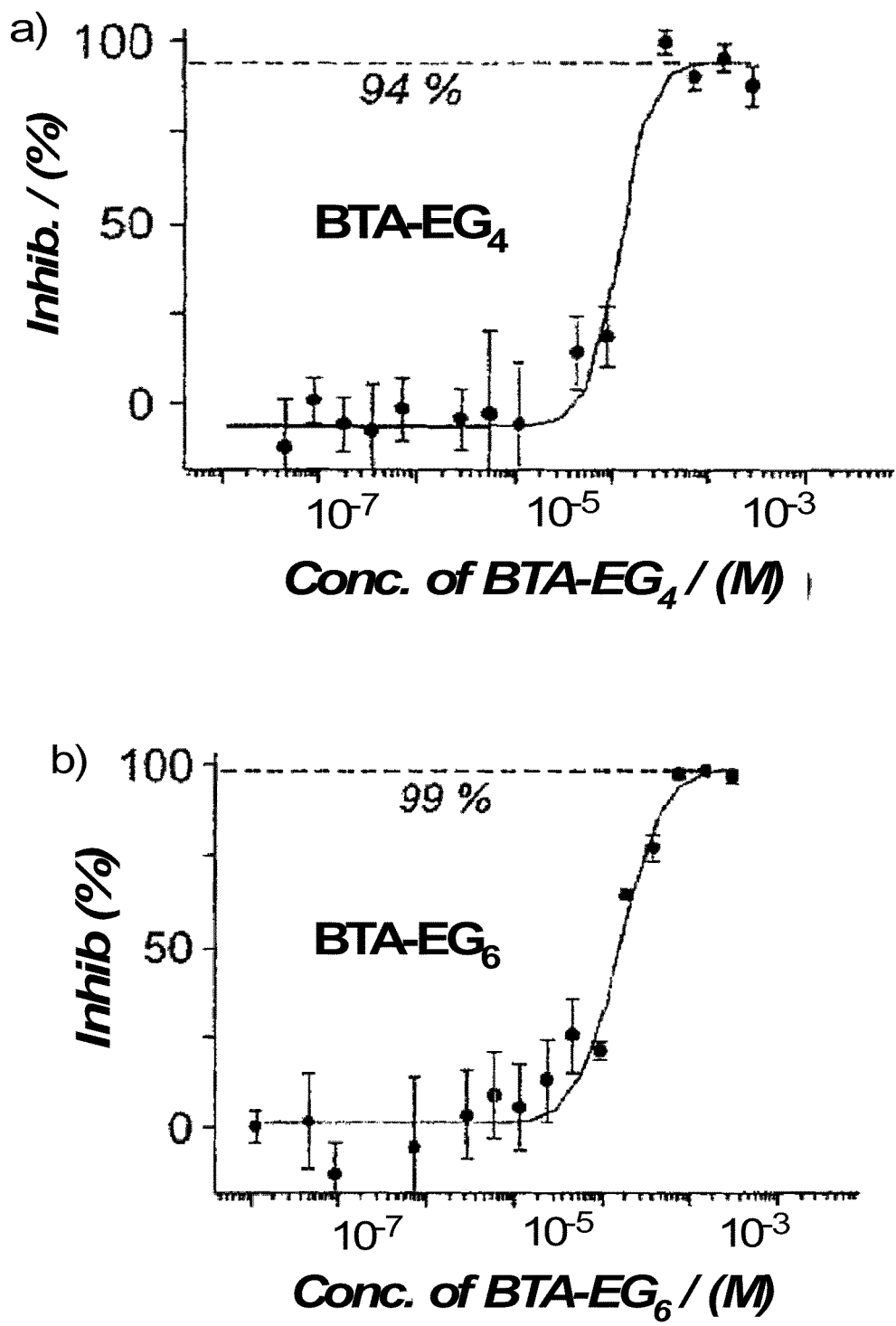
FIG. 5. Inhibition (Inhb.) of IgG-Aβ fibril interactions using small molecules. Aβ fibrils were incubated with a solution of a monoclonal anti-Aβ IgG (clone 6E10) prior to exposure to solutions of a) BTA-EG$_4$; and b) BTA-EG$_6$. Note: the x-axis was plotted in a logarithmic scale for better visualization of the data.

When the inhibition of the catalase-A-beta fibril interactions with the inhibition of the IgG-A-beta fibril interactions was compared using the two BTA derivatives, however, comparable results were observed in terms of maximal inhibition. This result was somewhat surprising in that the monoclonal IgG (clone 6E10) was raised against residues 3-8 of A-beta peptides, which is a solvent exposed region of A-beta. (G. Y. Wen, S. Y. Yang, W. Kaczmarski, X. Y. He, K. S. Pappas, *Brain Res.* 2002, 954(1), 115-122) Since an experimentally significant difference for inhibition of the IgG-A-beta fibril interactions with BTA-$EG_4$ compared to BTA-$EG_6$ was observed (FIG. 5), it is possible that the size of the oligoethylene glycol chain attached to the BTA may play a role in the inhibition of this monoclonal IgG with the A-beta fibrils. Thus depending on the particular A-beta-binding protein, both the BTA and oligoethylene glycol components of the small molecules may play a significant role for inhibiting protein-amyloid interactions. The general observation that the BTA compounds showed significantly improved efficacy for inhibiting protein-amyloid interactions, in terms of total inhibition compared to ThT, might be due to potential differences in binding sites for BTA and ThT along the fibril axis. (Powell, A. J., et al., *J. Mol. Biol.* 2000:303:311-327)

Example 8

Synthesis of BTA Compounds

1-Iodo-3,6,9,12,15-pentaoxaheptadecanol and 1-iodo-3,6,9-trioxaundecanol were prepared according to literature. (H.

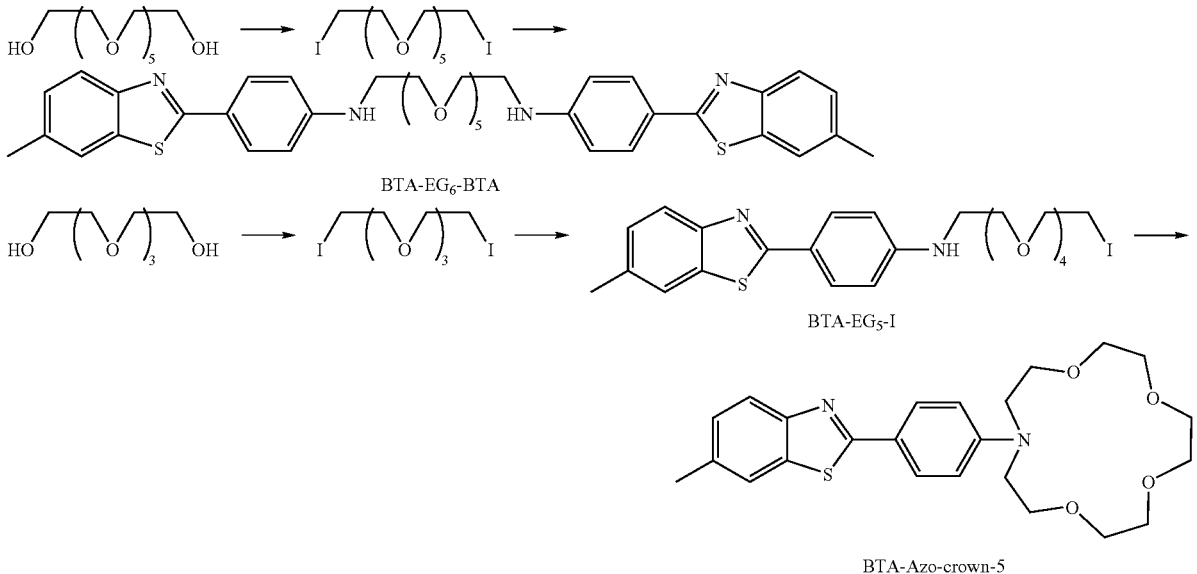

Bauer, F. Stier, C. Petry, A. Knorr, C. Stadler, H. A. Staab, *Eur. J. Org. Chem.* 2001, (17), 3255-3278.)

A representative procedure for the synthesis of the oligoethylene glycol derivatives of BTA is as follows: 1-Iodo-3,6,9,12,15-pentaoxaheptadecanol (0.18 g, 0.45 mmol) was coupled to 2-(p-aminophenyl)-6-methyl-benzothiazole (0.09 g, 038 mmol) with potassium carbonate (0.39 g, 2.8 mmol) in dry acetone (4 mL) under reflux conditions. The acetone was removed and the residue was taken up into dichloromethane, and separated from an insoluble precipitate (presumably excess potassium carbonate and potassium iodide). After the precipitate was removed by filtration, the solution was washed with brine, dried over sodium sulfate, and the solvent was removed under reduced pressure. The residue was purified via flash chromatography using 4% methanol in ethylacetate as the eluent to yield a yellow oil (isolated yield was 28%).

BTA-EG$_4$: $^1$H-NMR (400 MHz, CD$_3$OD): δ=2.44 (s, 3H), δ=3.34 (t, 2H, 2.7 Hz), δ=3.55 (t, 2H, 2.7 Hz), δ=3.60-3.69 (m, 10H), δ=3.68 (t, 2H, 2.7 Hz), δ=6.70 (d, 2H, 8.6 Hz), δ=7.26 (dd, 1H, 8.4 Hz, 1.2 Hz), δ=7.65 (d, 1H, 1.2 Hz), δ=7.74 (d, 1H, 8.4 Hz), δ=7.78 (d, 2H, 8.4 Hz); $^{13}$C-NMR (400 MHz, CD$_3$OD): δ=21.43, 43.93, 62.21, 70.91, 7135, 7137, 71.60, 71.62, 73.66, 113.34, 122.09, 122.36, 128.85, 129.86, 135.37, 136.04, 153.08, 153.11, 170.47; MS (ESI-positive): m/z 417.19 [MH$^+$] (calc. mass 416.18); FT-IR (on KBr in cm$^{-1}$): 816, 1095, 1181, 1340, 1453, 1483, 1604, 2858, 2913, 3394.

BTA-EG$_6$: $^1$H-NMR (400 MHz, CD$_3$OD): δ=2.47 (s, 3H), δ=3.71-3.53 (m, 24H), δ=6.74 (d, 2H, 8.4 Hz), δ=7.29 (d, 21-1, 8.4 Hz), δ=7.91-7.70 (m, 3H); $^{13}$C-NMR (400 MHz, CD$_3$OD): δ=21.46, 43.95, 62.16, 70.55, 7130, 71.39, 71.45, 71.46, 71.47, 71.51, 71.53, 71.56, 73.56, 113.38, 122.24, 122.38, 128.86, 129.89, 135.24, 136.04, 152.93, 153.08, 170.33; MS (ESI-positive): m/z 505.25 [MH$^+$] and 527.20 [MNa$^+$] (calc. mass 504.23); FT-IR (on KBr in cm$^{-1}$): 820, 1097, 1184, 1260, 1345, 1455, 1481, 1610, 2868, 2919, 3356.

Synthesis of BTA-EG$_6$-BTA 1,17-diiodo-3,6,9,12,15-pentaoxaheptadecane and 1,14-diiodo-3,6,9,12-tetraoxatetradecane were prepared according to literature. (H. Bauer, F. Stier, C. Petry, A. Knorr, C. Stadler, H. A. Staab, *Eur. J. Org. Chem.* 2001, (17), 3255-3278)

1,17-diiodo-3,6,9,12,15-pentaoxaheptadecane was coupled to 2-(p-aminophenyl)-6-methyl-benzothiazole with potassium carbonate in dry acetone under reflux conditions. The acetone was removed and the residue was taken up into dichloromethane, and separated from an insoluble precipitate (presumably excess potassium carbonate and potassium iodide). After the precipitate was removed by filtration, the solution was washed with brine, dried over sodium sulfate, and the solvent was removed under reduced pressure. The residue was purified via flash chromatography using 4% methanol in ethylacetate as the eluent to yield a yellow oil.

BTA-EG$_6$-BTA: $^1$H-NMR (400 MHz, CD$_3$OD): δ=2.43 (s, 6H), δ=3.21-3.29 (m, 12H), &=3.71-3.53 (m, 8H), δ=4.01-4.07 (m, 4H), δ=6.67 (d, 2H, 8.4 Hz), δ=7.27 (d, 2H, 8.4 Hz), δ=7.91-7.70 (m, 3H); MS (ESI-positive): m/z 727.24 [MH$^+$] and 749.18 [MNa$^+$] (calc. mass 726.4).

1,17-Iodo-3,6,9,12-tetraoxatetradecane (1.0 g, 2.2 mmol) was coupled to 2-(p-aminophenyl)-6-methyl-benzothiazole (3.7 g, 2.2 mmol) with potassium carbonate (4.8 g, 34.9 mmol) in dry THF under reflux conditions. The THF was removed and the residue was taken up into dichloromethane, and separated from an insoluble precipitate (presumably excess potassium carbonate and potassium iodide). After the precipitate was removed by filtration, the solution was washed twice with water, dried over sodium sulfate, and the solvent was removed under reduced pressure. The residue was purified via flash chromatography using a mixture of dichloromethane/ethylacetate (7:3) as the eluent to yield a yellow oil (yield 24%).

BTA-EG$_5$-I: $^1$H-NMR (500 MHz, CD$_3$OD): δ=2.42 (s, 3H), δ=3.20 (t, 2H, J=6.8 Hz), δ=3.58-3.65 (m, 14H), δ=3.67 (t, 2H, J=6.8 Hz), δ=3.69 (t, 2H, δ=6.8 Hz), δ=6.62 (d, 2H, 8.5 Hz), δ=7.20 (d, 2H, 8.5 Hz), δ=7.58 (s, 1H,), δ=7.81 (d, 2H, 8.0 Hz), δ=7.84 (d, 21-1, 9.0 Hz), MS (ESI-positive): m/z 571.04 [MH$^+$] and 593.00 [MNa$^+$] (calc. mass 570.23).

BTA-Eg$_5$-1 (50 mg, 0.09 mmol) and lithium hydroxide (4.2 mg, 0.17 mmol) were dissolved in 10 mL of THF and refluxed for 20 h. The solution was cooled to room temperature and the solvent was removed under reduced pressure. The residue was taken up in a mixture of dichloromethane/ethylacetate (50:50) and filtered through silica gel to remove excess lithium hydroxide. The crude material was purified via silica gel flash chromatography using a mixture of dichloromethane/ethylacetate (70:30) as the eluent to yield 22 mg of a yellowish oil (yield 56%).

Figure 8:
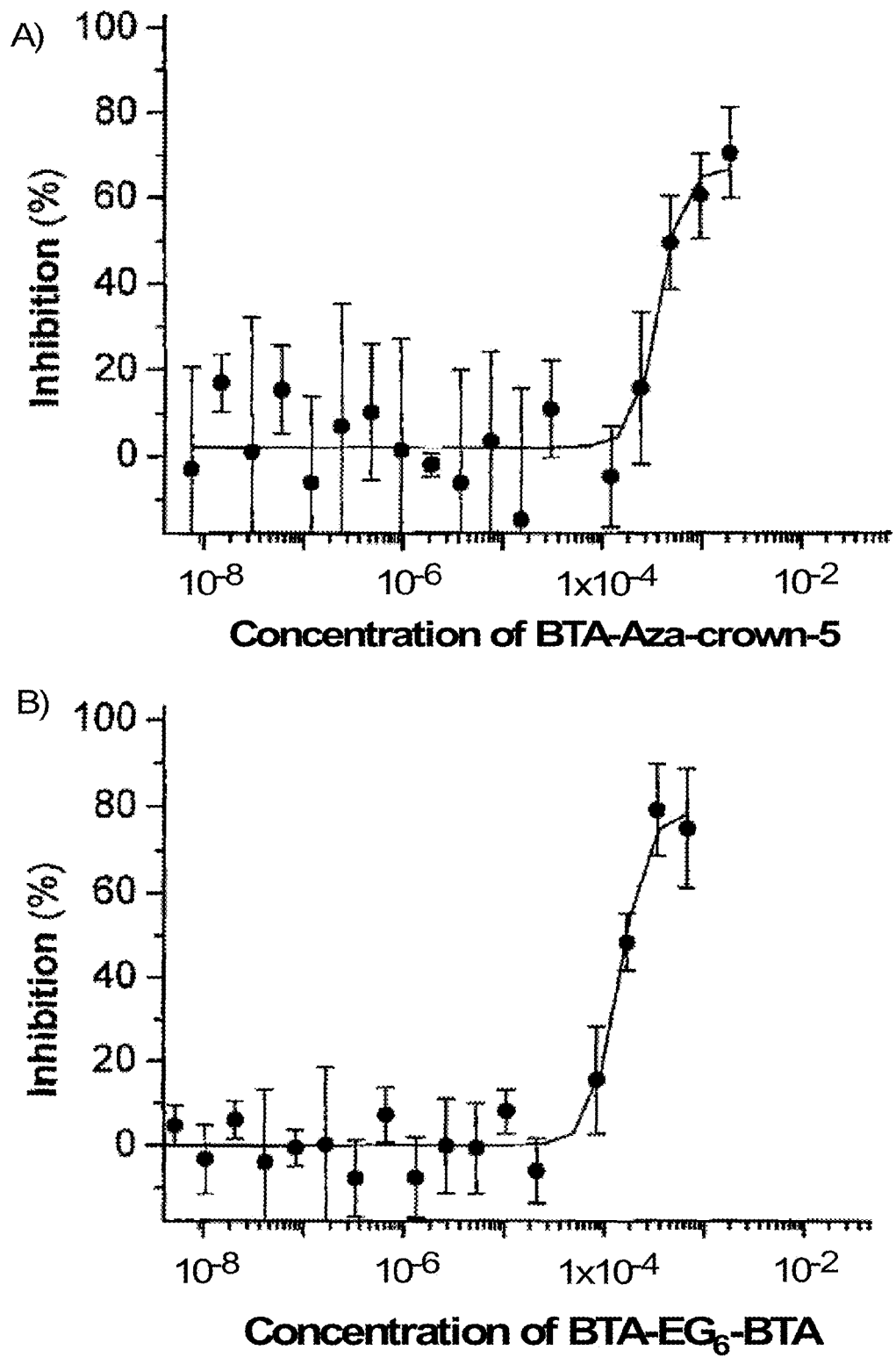
FIG. 8. Inhibition of ABAD-A-β fibril interaction with BTA Aza-crown-5 (A) and BTA-EG$_6$-BTA.

BTA-Azocrown-5: $^1$H-NMR (400 MHz, CD$_3$OD): δ=2.47 (s, 3H), δ=3.59-3.70 (m, 16H), δ=3.79 (t, 4H, 6.0 Hz), δ=6.72 (d, 2H, 8.8 Hz), δ=7.26 (s, 2H), δ=7.63 (s, 1H), δ=7.85 (d, 1H, J=8.4 Hz), δ=7.90 (d, 2H, J=8.8 Hz); MS (ESI-positive): m/z 443.23 [MH$^+$] and 465.17 [MNa$^+$] (talc. mass 442.19);

Inhibition graphs of BTA-EG$_6$-BTA and BTA-Azocrown-5 are presented in FIG. 8.

Example 9

Inhibition Assays

Procedure for Inhibition Assays:
All incubation steps were done at 25° C. unless stated otherwise. Phosphate buffered saline (PBS, 10 mM sodium phosphate, 138 mM sodium chloride, 2.7 mM potassium chloride, pH 7.4) and potassium phosphate buffer (KPi, 200 mM potassium phosphate, 10 mM mercaptoethanol, pH 6.6) were prepared fresh for each experiment.

Growth of A-beta fibrils: Aβ fibrils were grown from synthetic Aβ (1-42) peptides by incubating the peptides (74 µM) in ultrapure water at 37° C. for 72 hours. Fibrils were characterized by electron and scanning probe microscopy. (P. Inbar, J. Yang, *Bioorg. Med. Chem. Lett.* 2006, 16(4), 1076-1079).

Recombinant expression of ABAD: ABAD was obtained from an external contract laboratory (e.g., Commonwealth Biotechnologies, Inc., Richmond, Va.) that cloned the DNA for ABAD (genebank number AF035555), and expressed and purified the protein from a 1 L culture of *E. coli* using a literature protocol. (Yan., S. D., et al., *J. Biol. Chem.* 1999: 274:2145-2156); S. D. Yan, Y. Shi, A. Zhu, J. Fu, H. Zhu, Y. Zhu, L. Gibson, E. Stem, K. Collison, F. Al-Mohanna, S. Ogawa, A. Roher, S. G. Clarke, D. M. Stern, *J. Biol. Chem.* 1999, 274(4), 2145-2156; S. D. Yan, et al., *Biochim. Biophys. Acta* 2000:1502:145-157). N-terminal sequencing using 15 cycles of Edman degradation was consistent with the predicted sequence of the protein.

Qualitative determination of the binding of Aβ fibrils to catalase and ARAD: The wells of a 96 well plate were coated with catalase or ABAD by incubating each well for 2 hours with 50 µL of a solution of catalase (24 nM in 1% BSA/PBS buffer) or ABAD (1.0 µM, in 1% BSA/KPi buffer). After removal of the solutions containing excess catalase or ABAD, all wells were blocked for 60 min. using 300 µL of a solution containing 1% BSA in PBS buffer to suppress non-specific adsorption of IgGs to the wells. Wells were washed with 300 µL of PBS buffer and incubated for 2 hours with 50 µL of solutions containing Aβ fibrils (various concentrations were obtained by diluting a stock solution of 49 µM A-beta fibrils) in 1% BSA/PBS buffer. Wells were washed twice with 300 µL of PBS buffer and each well was incubated for an hour with 50 µL of a solution containing a mouse monoclonal anti-Aβ IgG (clone 6E10, lot #145271, 1.1 nM in 1% BSA/PBS).

The amount of bound monoclonal IgGs was quantified by removing the excess solution, washing the wells twice with 300 µL of PBS buffer and by incubating for 45 minutes with 50 µL of a polyclonal secondary rabbit IgG (anti-mouse IgG, 6.8 nM in 1% BSA/PBS) conjugated with alkaline phosphatase, followed by two washes with 300 µL of PBS buffer. The relative amount of secondary IgG bound in each well was quantified by adding 50 µL of a solution containing p-nitrophenyl phosphate (NPP, 2.7 mM, in 0.1 M diethanol amine/ 0.5 mM magnesium chloride, pH 9.8) to each well. The enzymatic hydrolysis reaction of NPP by alkaline phosphatase was quenched after 45 min. by adding 50 µL of 0.25 N sodium hydroxide solution to each well and quantifying the concentration of p-nitrophenoxide at 405 nm using a UV-Vis microplate reader. Each data point from this assay represents the average of five independent measurements. Error bars represent standard deviations. Graphs were normalized, plotted and fitted with the sigmoidal curve fitting option in Origin 6.0 (Microcal Software, Inc., Northhampton, Mass., USA).

Inhibition of antiAβ IgG-A-beta fibril interactions using small molecules: The wells of a 96 well plate were coated with fibrils formed from A-beta peptides by incubating each well for 2 hours with 50 µL of a 1.3 µM solution of Aβ fibrils in PBS. After removal of solutions containing excess A-beta fibrils, all wells were blocked for 60 min. using 300 µL of a solution containing 1% BSA in PBS buffer.

The BSA/PBS solutions were discarded and the wells were washed with 300 µL of PBS buffer and incubated with 50 µL of an anti-An IgG (clone 6E10, Lot #145271, 1.1 nM in 1% BSA/PBS) for 1 hour. After removal of solutions containing excess IgG, 50 µL solutions of small molecules in 1% BSA/ PBS buffer (for ThT and BTA-EG$_6$) or 5% DMSO/1% BSA/ PBS (for BTA-EG$_4$) (various concentrations were obtained by diluting a stock solution) were incubated in the wells for 12 hours, followed by removal of solutions containing excess small molecule. The amount of monoclonal IgG present in the wells was quantified as described in the procedure for determining the binding of Aβ fibrils to catalase and ABAD.

Inhibition of catalase-A-beta fibril or ABAD-A-beta fibril interactions using small molecules: The wells of a 96 well plate were coated with fibrils formed from A-beta peptides by incubating each well for 2 hours with 50 µL of a 1.3 µM solution of Aβ fibrils in PBS. After removal of solutions containing excess A-beta fibrils, all wells were blocked for 60 min. using 300 µL of a solution containing 1% BSA in PBS buffer.

The BSA/PBS solutions were discarded and the wells were washed with 300 µL of PBS buffer and incubated with 50 µL of a human catalase solution (0.20 µM, in 1% BSA/PBS buffer) or 50 µL of an ABAD solution (10 in 1% BSA/KPi) at 37° C. for 3 hours or at 25° C. for 2 hours respectively. After removal of solutions containing excess catalase or ABAD, 50 solutions of small molecules in 1% BSA/PBS buffer (for ThT and BTA-EG$_6$) or 5% DMSO/1% BSA/PBS (for BTA-EG$_4$) (various concentrations were obtained by diluting a stock solution) were incubated in the wells for 12 hours, followed by removal of solutions containing excess small molecule.

The wells were then washed twice with 300 µL of a solution containing 1% BSA in PBS and each well was incubated for 1 hour with 50 µL of a solution of a monoclonal mouse anti-catalase IgG (clone 1A1, lot #93195, 2.2 nM in 1% BSA/PBS) or 50 µL of a solution of a monoclonal mouse anti-ABAD IgG (clone 5F3, lot #103614, 1.3 nM in 1% BSA/PBS buffer). The amount of monoclonal IgG present in the wells was quantified as described in the procedure for determining the binding of Aβ fibrils to catalase and ABAD.

Example 10

Diffusion across Cell Membranes and the Blood Brain Barrier

In order to assess the potential utility of BTA-EG$_4$ and BTA-EG$_6$ as probes to study protein-amyloid interactions in cellular assays, the likeliness of the BTA derivatives to passively diffuse across cell membranes and the Blood-Brain-Barrier (BBB) was estimated. (C. A. Lipinski, F. Lombardo, B. W. Dominy, P. J. Feeney, *Adv. Drug Delivery Rev.* 1997, 23(1-3), 3-25) Table 1 lists some of the intrinsic properties of ThT, BTA-EG$_4$, and BTA-EG$_6$ compared to some well-known parameters for the biocompatibility of small molecules. (W. P. Walters, A. A. Murcko, M. A. Murcko, *Curr. Opin. Chem. Bio.* 1999, 3(4), 384-387) The log P$_{octanol/water}$ was determined for the molecule.

15 µM solutions of small molecule were prepared in 5 mL PBS buffer. 5 mL of octanol was added to each aqueous solution of small molecule and the biphasic layers were mixed by rapid vortexing. The mixture was then centrifuged at 250×g to facilitate the formation of two clear layers. The layers were separated and the absolute concentrations of small molecules in each layer were quantified by measuring the absorbance of the layers at 348 nm and 412 nm for the BTA derivatives and ThT, respectively. The molar extinction coefficient of ThT and the BTA derivatives in octanol and PBS buffer were determined by comparison to standard calibration curves of known quantities of small molecules dissolved in octanol and PBS buffer. The partition coefficient was expressed as logarithm of the ratio of the concentration in octanol divided by the concentration in PBS (i.e., log P).

Topological polar surface areas were estimated using Molinspiration Cheminformatics software. This web-based software is available on the WorldWideWeb at molinspiration.com/cgi-bin/properties.

From the measured log P$_{octanol/water}$ (Klunk, W. E., et al., *Life Sci.* 2001, 69:1471-1484) and calculated polar surface areas (a) D. E. Clark, J. Pharm. Sci. 1999, 88(8), 815-821; b) J. Kelder, P. D. J. Grootenhuis, D. M. Bayada, L. P. C. Delbressine, J.-P. Ploemen, Pharm. Res. 1999, 16(10), 1514-1519; P. Ertl, B. Rohde, P. Selzer, J. Med. Chem. 2000, 43(20), 3714-3717) shown in Table 1, ThT may be predicted to have relatively poor biocompatibility for use in cellular or in in vivo studies (previous reports agree with this prediction (Mathis, C. A., et al., *Curr. Pharm. Design* 2004, 10:1469-1492). The two oligoethylene glycol derivatives of BTA, however, may be more suitable for cellular and in vivo studies than ThT since they fall within the measured and calculated parameters for permeability to cells and the BBB. The uptake of these molecules in the brain has yet to be determined.

TABLE 2

Chemical properties of ThT, BTA-EG$_4$, and BTA-EG$_6$ to assess their likeliness for passive diffusion through cell membranes and through the Blood-Brain-Barrier. (Li, L., et al., *Biophys. J.* 1999, 76: 2871-78; Lipinski, C. A., et al., *Adv. Drug Delivery Rev.* 1997, 23: 3-25).

| Compound | Molecular weight | Log (P)[a] | # of H-bond acceptors | # of H-bond donors | TPSA[b] |
|---|---|---|---|---|---|
| Desired properties[c] | <500 g/mol | 1-3 (ideal ~2) | <10 | <5 | <120 Å$^2$ |
| BTA-EG$_4$ | 418 g/mol | 1.05 | 6 | 2 | 91.3 Å$^2$ |
| BTA-EG$_6$ | 504 g/mol | 1.43 | 8 | 2 | 72.8 Å$^2$ |
| ThT | 319 g/mol | 0.43 | 1 | 0 | 7.1 Å$^2$ |

[a] determined by octanol-water partitioning
[b] topological polar surface area (Clark, D. E., et al., *J. Pharm. Sci.* 1999, 88: 815-821; Kelder, J., et al., *Pharm. Res.* 1999, 16: 1514-1519), calculated with Molinspiration Cheminformatics software
[c] optimal properties for good permeability across lipophilic biological barriers In other examples of blood brain barrier penetration studies, rabbits are injected with rifampin and the amount in the blood serum and the celebrospinal fluid is determined after 2,3,6 and 12 hours. Samples are taken under anesthesia as in, for example, Chan, K., et al., *Asia Pacific J. Pharm.* 1986, 1(1), 41-45.

Example 11

General Procedure for Detecting the Binding of Small Molecules to Amyloid Fibrils All incubation steps are done at 25° C. unless stated otherwise. Phosphate buffered saline (PBS, 10 mM sodium phosphate, 138 mM sodium chloride, 2.7 mM potassium chloride, pH 7.4) are prepared fresh for each experiment.

Wells of a 96 well plate are coated with fibrils formed from various amyloid forming peptides (such as α-synuclein, huntingtin, amylin . . . ) by incubating each well for 2 hours with 50 µL of a solution of amyloid fibrils in PBS (concentration 0.05-5 µM). After removal of solutions containing excess fibrils, all wells are blocked for 30 min. using 300 µL of a solution containing 1% BSA in PBS buffer.

The BSA/PBS solutions are discarded and the wells are washed with 300 µL of PBS buffer and 50 µL solutions of small molecules in 1% BSA/PBS buffer (various concentrations can be obtained by diluting a stock solution) are incubated in the wells for 12 hours, followed by removal of solutions containing excess small molecule. The wells are washed twice with 300 µL, PBS buffer and incubated with 50 µL of a mouse monoclonal anti-amyloid IgG (IgGs are commercially available from e.g., Abcam, Inc, Cambridge, Mass.) and are raised against the fibril deposited into the wells. Concentrations are optimized and might range from 0.05-10 nM in 1% BSA/PBS) for 1 hour. After removal of solutions containing excess IgG, the relative amount of secondary IgG bound in each well is quantified by adding 50 µl, of a solution containing p-nitrophenyl phosphate (NPP, 2.7 mM, in 0.1 M diethanol amine/0.5 mM magnesium chloride, pH 9.8) to each well. The enzymatic hydrolysis reaction of NPP by alkaline phosphatase is quenched after 45 min. by adding 50 µL of 0.25 N sodium hydroxide solution to each well and quantifying the concentration of p-nitrophenoxide at 405 nm using a UV-Vis microplate reader. Each data point from this assay will represent the average of five independent measurements. Error bars will represent standard deviations. Graphs can be normalized, plotted and fitted with the sigmoidal curve fitting option in Origin 6.0 (Microcal Software, Inc., Northhampton, Mass., USA).

Specific Example for Detection of the Binding of Congo Red to Alpha-Synuclein:

The wells of a 96 well plate were coated with fibrils formed from α-synuclein peptides by incubating each well for 2 hours with 50 μL of a solution of a-synuclein amyloid fibrils in PBS (concentration 0.23 μM). After removal of solutions containing excess fibrils, all wells were blocked for 30 min. using 300 μL of a solution containing 1% BSA in PBS buffer.

The BSA/PBS solutions were discarded and the wells were washed with 300 μL of PBS buffer and 50 μL solutions of congo red in 1% BSA/PBS buffer (various concentrations were obtained by diluting a stock solution) were incubated in the wells for 12 hours, followed by removal of solutions containing excess small molecule. The wells were washed twice with 300 μL PBS buffer and incubated with 50 μL of a mouse monoclonal anti-α-synuclein IgG (clone [4B12], Abcam, Inc., Cambridge, Mass., 0.7 nM in 1% BSA/PBS) for 1 hour. After removal of solutions containing excess IgG, the relative amount of secondary IgG bound in each well was quantified by adding 50 μL of a solution containing p-nitrophenyl phosphate (NPP, 2.7 mM, in 0.1 M diethanol amine/0.5 mM magnesium chloride, pH 9.8) to each well. The enzymatic hydrolysis reaction of NPP was quenched by alkaline phosphatase after 45 min. by adding 50 μL, of 0.25 N sodium hydroxide solution to each well and quantifying the concentration of p-nitrophenoxide at 405 nm using a UV-Vis microplate reader. Each data point from this assay represents the average of five independent measurements. Error bars represent standard deviations. Graphs were normalized, plotted and fitted with the sigmoidal curve fitting option in Origin 6.0 (Microcal Software, Inc., Northhampton, Mass., USA).

Figure 9:
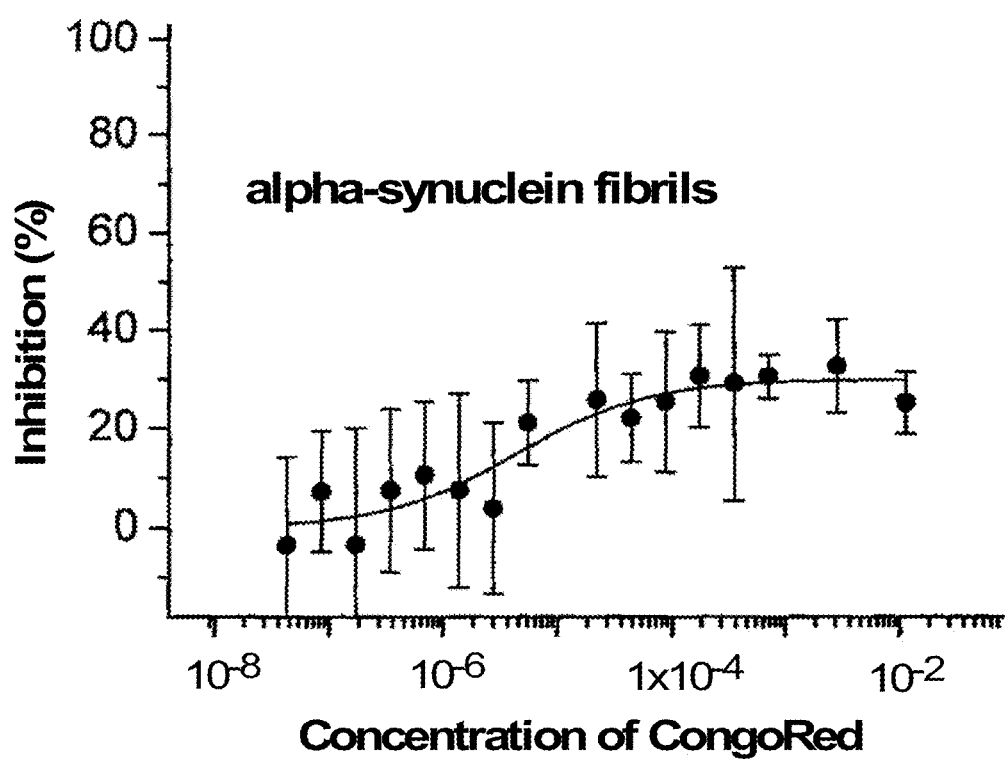
FIG. 9: Inhibition of alpha-synuclein fibril interaction with CongoRed.

An inhibition graph of alpha-synuclein fibrils with Con-goRed is shown in FIG. 9.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Singular forms "a", "an", and "the" include plural reference unless the context clearly dictates otherwise. Thus, for example, reference to "a subset" includes a plurality of such subsets, reference to "a nucleic acid" includes one or more nucleic acids and equivalents thereof known to those skilled in the art, and so forth. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies that are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A method of inhibiting binding between A-beta fibrils and amyloid-binding proteins, said method comprising contacting A-beta fibrils with a compound of formula I:

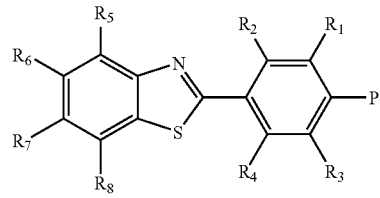

wherein $R_1$-$R_8$ are selected from the group consisting of hydrogen, deuterium, tritium, fluoride, chloride, bromide, iodide, hydroxide, amino, methylamino, dimethylamino, trimethylammonium, methyl, ethyl, methoxy, ethoxy, fluoromethyl, difluoromethyl and trifluoromethyl, wherein at least one of $R_5$-$R_8$ and one of $R_1$-$R_4$ is H; and P is selected from the group consisting of

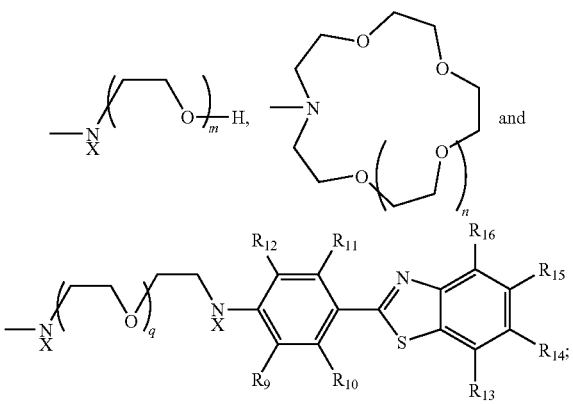

wherein
m is an integer between 1 and 20;
n is 0, 1, or 2;
q is an integer between 1 and 20;
$R_9$-$R_{16}$ are selected from the group consisting of hydrogen, deuterium, tritium, fluoride, chloride, bromide, iodide, hydroxide, amino, methylamino, dimethylamino, trimethylammonium, methyl, ethyl, methoxy, ethoxy, fluoromethyl, difluoromethyl and trifluoromethyl, wherein at least one of $R_9$-$R_{12}$ and one of $R_{13}$-$R_{16}$ is H;

X is hydrogen, methyl, or ethyl, thereby inhibiting binding between A-beta fibrils and amyloid binding proteins.

2. A method of inhibiting binding between A-beta fibrils and a second binding molecule, said method comprising contacting A-beta fibrils with a sufficient amount of a first binding molecule to inhibit the interactions of said A-beta fibrils with a second binding molecule.

3. The method of claim 2, wherein said second binding molecule is a cellular component in the brain.

4. The method of claim 2, wherein said second binding molecule is selected from the group consisting of catalase, ABAD, and RAGE.

5. The method of claim 2, wherein said first binding molecule is selected from the group consisting of Congo Red, and Thioflavin T.

6. The method of claim 5, wherein said first binding molecule is a compound of formula I:

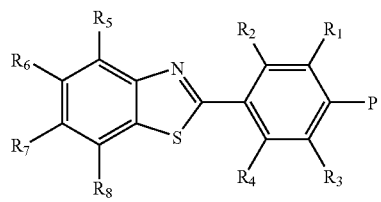

wherein $R_1$-$R_8$ are selected from the group consisting of hydrogen, deuterium, tritium, fluoride, chloride, bromide, iodide, hydroxide, amino, methylamino, dimethylamino, trimethylammonium, methyl, ethyl, methoxy, ethoxy, fluoromethyl, difluoromethyl and trifluoromethyl, wherein at least one of $R_5$-$R_8$ and one of $R_1$-$R_4$ is H; and P is selected from the group consisting of

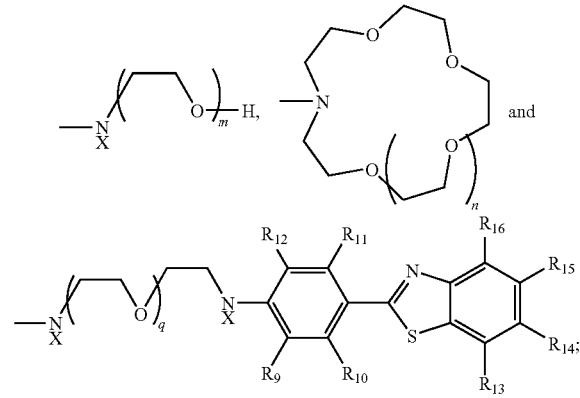

wherein
m is an integer between 1 and 20;
n is 0, 1, or 2;
q is an integer between 1 and 20;
$R_9$-$R_{16}$ are selected from the group consisting of hydrogen, deuterium, tritium, fluoride, chloride, bromide, iodide, hydroxide, amino, methylamino, dimethylamino, trimethylammonium, methyl, ethyl, methoxy, ethoxy, fluoromethyl, difluoromethyl and trifluoromethyl, wherein at least one of $R_9$-$R_{12}$ and one of $R_{13}$-$R_{16}$ is H; and
X is hydrogen, methyl, or ethyl.

7. A method for detecting an amyloid deposit in an individual, said method comprising administering an A-beta fibril-binding compound to an individual and detecting the binding of said compound to amyloid deposits in said individual, wherein said compound is selected from the group consisting of Congo Red, Fluoroscein, Acridine Orange, Diamino Acridine, Crystal Violet, Thioflavin T, Oxytetracycline, Tetracycline, Chlortetracycline, Tannic Acid, Rosmarinic Acid, (+)-Catechin, (−)-Nicotine, Morin, Serotonin, Dopamine, Curcumin, (R)-Ibuprofen, (S)-Naproxen, Rifampin, D-(+)-Trehalose, D-nicotine, pegylated derivatives of 1-(p-aminophenyl)-6-methylbenzothiazole, and a compound of formula I:

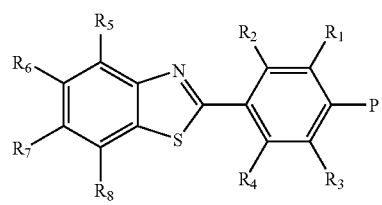

wherein $R_1$-$R_8$ are selected from the group consisting of hydrogen, deuterium, tritium, fluoride, chloride, bromide, iodide, hydroxide, amino, methylamino, dimethylamino, trimethylammonium, methyl, ethyl, methoxy, ethoxy, fluoromethyl, difluoromethyl and trifluoromethyl, wherein at least one of $R_5$-$R_8$ and one of $R_1$-$R_4$ is H; and P is selected from the group consisting of

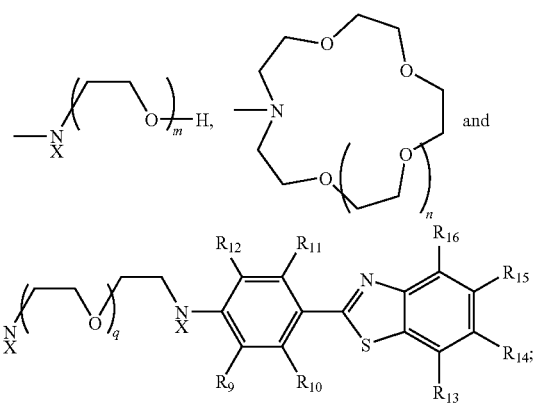

wherein
m is an integer between 1 and 20;
n is 0, 1, or 2;
q is an integer between 1 and 20;
$R_9$-$R_{16}$ are selected from the group consisting of hydrogen, deuterium, tritium, fluoride, chloride, bromide, iodide, hydroxide, amino, methylamino, dimethylamino, trimethylammonium, methyl, ethyl, methoxy, ethoxy, fluoromethyl, difluoromethyl and trifluoromethyl, wherein at least one of $R_9$-$R_{12}$ and one of $R_{13}$-$R_{16}$ is H; and
X is hydrogen, methyl, or ethyl.

* * * * *